(12) United States Patent
Hsu

(10) Patent No.: US 10,709,643 B2
(45) Date of Patent: *Jul. 14, 2020

(54) TAMPER-PROOF PILL DISPENSING SYSTEM AND METHODS OF USE

(71) Applicant: John Hsu, Rowland Heights, CA (US)

(72) Inventor: John Hsu, Rowland Heights, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/780,143

(22) Filed: Feb. 3, 2020

(65) Prior Publication Data

US 2020/0170889 A1 Jun. 4, 2020

Related U.S. Application Data

(63) Continuation of application No. 16/513,187, filed on Jul. 16, 2019, now Pat. No. 10,588,824, which is a (Continued)

(51) Int. Cl.

| | | |
|---|---|---|
| *A61J 7/04* | (2006.01) |
| *G07F 11/62* | (2006.01) |
| *G06Q 20/12* | (2012.01) |
| *G16H 40/63* | (2018.01) |
| *G16H 20/13* | (2018.01) |

(Continued)

(52) U.S. Cl.
CPC ........... *A61J 7/0418* (2015.05); *A61J 7/0076* (2013.01); *G06Q 20/127* (2013.01); *G07F 11/62* (2013.01); *G07F 17/0021* (2013.01); *G07F 17/0092* (2013.01); *G16H 20/13* (2018.01);

(Continued)

(58) Field of Classification Search
CPC .................................................. G07F 17/0092
See application file for complete search history.

(56) References Cited

U.S. PATENT DOCUMENTS

| | | |
|---|---|---|
| 6,304,797 B1 | 10/2001 | Shusterman |
| 7,366,675 B1 | 4/2008 | Walker et al. |

(Continued)

FOREIGN PATENT DOCUMENTS

WO 2016059428 A2 4/2016

OTHER PUBLICATIONS

International Search Report and Written Opinion, PCT/US2018/015766, dated Apr. 6, 2018.

(Continued)

*Primary Examiner* — Timothy R Waggoner
(74) *Attorney, Agent, or Firm* — Entralta P.C.; Justin G. Sanders; Peter D. Weinstein

(57) ABSTRACT

A pill dispensing system and associated methods are configured for managing the distribution of pills to a patient. In at least one embodiment, an at least one tamper-proof pill storage container provides an at least one pill magazine positioned within a housing of the pill storage container and configured for storing and selectively dispensing a plurality of pills through a pill outlet provided by the housing. A patient application, residing in memory on an at least one patient device under the control of the patient, is in selective communication with the at least one pill storage container. An at least one monitoring device is in selective communication with the patient application, the at least one monitoring device configured for assisting the patient application with monitoring an at least one vital of the patient.

20 Claims, 22 Drawing Sheets

Related U.S. Application Data continuation of application No. 16/144,685, filed on Sep. 27, 2018, now Pat. No. 10,426,707, which is a continuation-in-part of application No. 15/882,803, filed on Jan. 29, 2018, now abandoned.

(60) Provisional application No. 62/451,634, filed on Jan. 27, 2017.

(51) Int. Cl.
*G07F 17/00* (2006.01)
*A61J 7/00* (2006.01)

(52) U.S. Cl.
CPC ............ *G16H 40/63* (2018.01); *A61J 7/0463* (2015.05); *A61J 7/0481* (2013.01); *A61J 2200/30* (2013.01)

(56) References Cited

U.S. PATENT DOCUMENTS

| | | | |
|---|---|---|---|
| 9,542,534 | B1 | 1/2017 | Ducatt et al. |
| 9,675,523 | B2 | 6/2017 | Ducatt et al. |
| 9,953,140 | B2 | 4/2018 | McLean et al. |
| 10,588,824 | B2 * | 3/2020 | Hsu .................. G16H 40/63 |
| 2003/0099158 | A1 | 5/2003 | De la Huerga |
| 2013/0110283 | A1 | 5/2013 | Baarman et al. |
| 2013/0195326 | A1 | 8/2013 | Bear et al. |
| 2014/0278510 | A1 | 9/2014 | McLean et al. |
| 2015/0359711 | A1 | 12/2015 | Ducatt et al. |
| 2016/0158107 | A1 * | 6/2016 | Dvorak ................ A61J 7/0084 241/25 |
| 2016/0283691 | A1 | 9/2016 | Ali |
| 2016/0374902 | A1 | 12/2016 | Govindasamy et al. |

OTHER PUBLICATIONS

International Search Report and Written Opinion, PCT/US2019/015010, dated May 23, 2019.

* cited by examiner

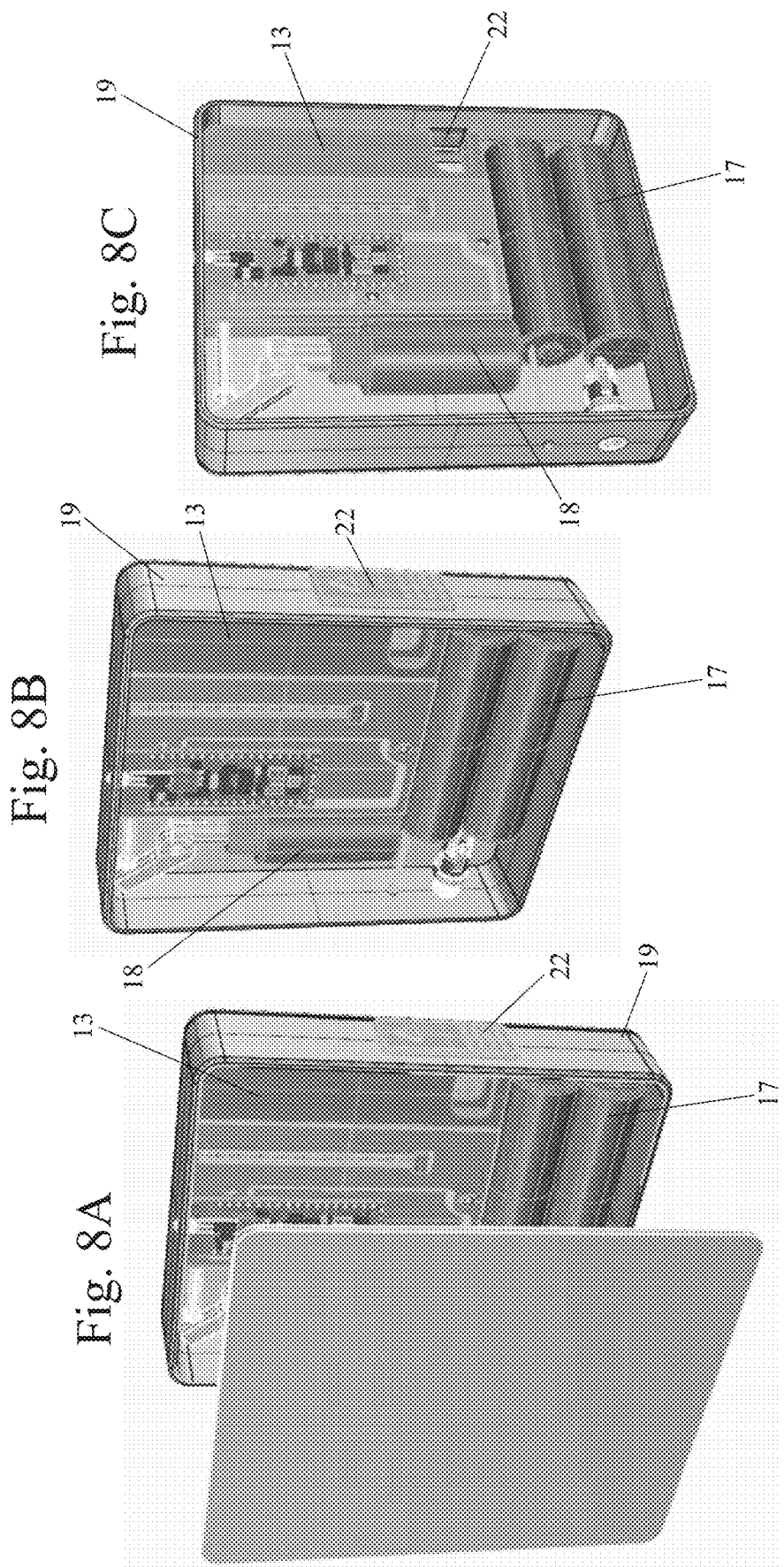

TAMPER-PROOF PILL DISPENSING SYSTEM AND METHODS OF USE

RELATED APPLICATIONS

This is a continuation application and so claims the benefit pursuant to 35 U.S.C. § 120 of a prior filed and co-pending U.S. non-provisional patent application Ser. No. 16/513,187, filed on Jul. 16, 2019, which itself is a continuation application of U.S. non-provisional patent application Ser. No. 16/144,685, filed on Sep. 27, 2018 (now U.S. Pat. No. 10,426,707, issued on Oct. 1, 2019), which is a continuation-in-part application of U.S. non-provisional patent application Ser. No. 15/882,803, filed on Jan. 29, 2018, which claims priority pursuant to 35 U.S.C. § 119(e) to and is entitled to the filing date of U.S. provisional patent application Ser. No. 62/451,634, filed on Jan. 27, 2017. The contents of the aforementioned applications are incorporated herein by reference.

BACKGROUND

The subject of this patent application relates generally to medication dispensing devices, and more particularly to a tamper-proof pill dispensing system and associated methods of use.

Applicant hereby incorporates herein by reference any and all patents and published patent applications cited or referred to in this application.

By way of background, opiods include prescription drugs such as oxycodone (OXYCONTIN®, OXECTA®, ROXICODONE®), oxycondone and acetaminophen (PERCOCET®, ENDOCET®, ROXICET®), hydrocodone (HYSINGLA ER®, ZOHYDRO ER®), hydrocodone and acetaminophen (LORCET®, LORTAB®, NORCO®, VICODIN®), hydromorphone (DILAUDID®), meperidine (DEMEROL®), methadone, codeine, morphine, and fentanyl as well as illegal drugs such as heroin. Studies have found that a person dies from an opioid overdose roughly every 20 minutes, and roughly 30,000 people die a year. It is an epidemic that difficult to treat. Over 90% of people who overdose on prescription painkillers continue to use them and this use cost the United States 78.5 billion dollars in 2013.

Government policies to limit opioids will not treat pain nor stem the addiction problem. It will worsen the problem for addicts and compliant patients. Those who cannot get opioids turn to heroin, which is becoming increasingly more dangerous with the addition of Car-Fentanyl. Studies from the CDC show that roughly 100 million people are taking opioids for chronic pain, and the government wants to limit their access to opioids. Those 100 million patients need a solution to prevent their opioids used for their treatment of pain from being taken away from them.

Doctors write prescriptions correctly; pharmacists fill prescriptions correctly; patients receive a bottle of opioids containing 30 to 120 pills of opioids, and therein lies the problem. The patient can take 1 pill or 120 pills. Patient compliance is a problem. This is further compounded by the sharing of opioids or sharing of excess opioid pills. Most of those who abuse prescription opioids obtain them for free from a friend or relative. However, those who are at highest risk of overdose (using prescription opioids non-medically 200 or more days a year) obtain them in ways that are different from those who use them less frequently. These people obtain opioids using their own prescriptions (27 percent), from friends or relatives for free (26 percent), buying from friends or relatives (23 percent), or buying from a drug dealer (15 percent). Those at highest risk of overdose are about four times more likely than the average user to buy the drugs from a dealer or other stranger.

Aspects of the present invention fulfill these needs and provide further related advantages as described in the following summary.

It should be noted that the above background description includes information that may be useful in understanding aspects of the present invention. It is not an admission that any of the information provided herein is prior art or relevant to the presently claimed invention, or that any publication specifically or implicitly referenced is prior art.

SUMMARY OF THE INVENTION

Aspects of the present invention teach certain benefits in construction and use which give rise to the exemplary advantages described below.

The present invention solves the problems described above by providing a pill dispensing system and associated methods configured for managing the distribution of pills to a patient. In at least one embodiment, an at least one tamper-proof pill storage container provides an at least one pill magazine positioned within a housing of the pill storage container and configured for storing and selectively dispensing a plurality of pills through a pill outlet provided by the housing. A patient application, residing in memory on an at least one patient device under the control of the patient, is in selective communication with the at least one pill storage container. An at least one monitoring device is in selective communication with the patient application, the at least one monitoring device configured for assisting the patient application with monitoring an at least one vital of the patient. In use, the system is configured for obtaining from the patient a security code and an at least one biometric marker associated with the patient. A prescription associated with the pills, including a dosage interval and a dosage quantity, is registered with the system. Upon the patient application determining that a dosage of the pills is available for the patient, based on the associated dosage interval, the patient application notifies the patient via at least one of an audible alert, a visual alert and a vibrational alert via the at least one patient device. The patient application then obtains from the patient the security code and the at least one biometric marker. Upon the patient application authenticating the security code and the at least one biometric marker, the patient application transmits a signal to the at least one pill storage container, instructing said pill storage container to distribute a quantity of pills equal to the associated dosage quantity. Upon the pill storage container distributing the pills to the patient, it transmits a signal back to the patient application, and the patient application schedules a future dosage of the pills based on the associated dosage interval. In the event the patient application determines that the at least one monitored vital is abnormal, the patient application notifies the patient via at least one of an audible alert, a visual alert and a vibrational alert via the at least one patient device, and temporarily suspends future dosages of the pills until the patient application determines that said monitored vital has returned to normal Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIGS. 8A-8C are further images of the exemplary pill storage container of FIGS. 7A-7C;

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION OF THE INVENTION

Figure 1:
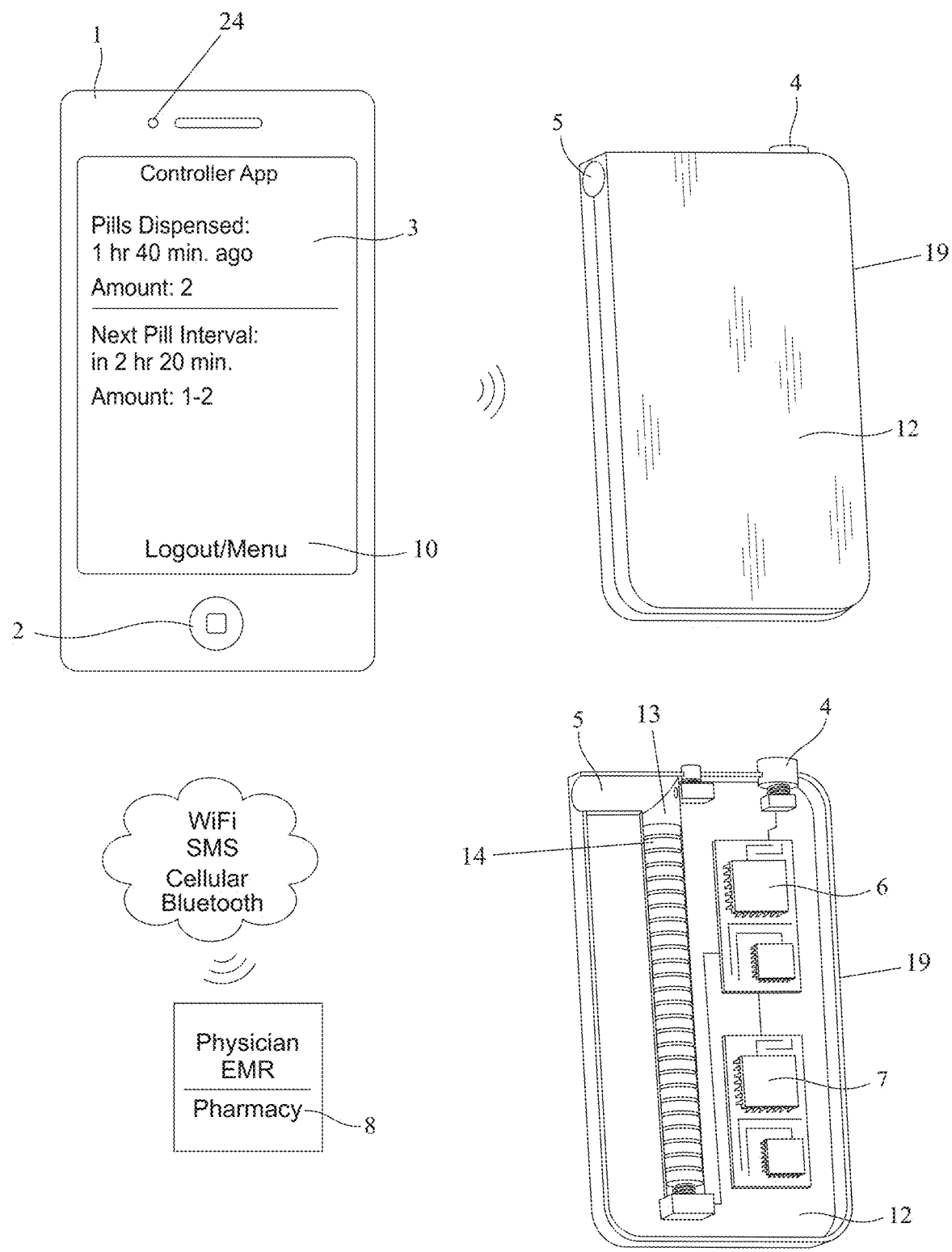
FIG. 1 is a simplified schematic view of an exemplary tamper-proof pill dispensing system, in accordance with at least one embodiment.

Turning now to FIG. 1, there is shown a simplified schematic view of an exemplary tamper-proof pill dispensing system 20 configured for managing the distribution of pills 14 to an at least one patient. In at least one embodiment, as discussed further below, the system 20 provides an at least one tamper-proof pill storage container 12, and an at least one patient device 1 in selective communication with the at least one pill storage container 12, with each of the pill storage container 12 and patient device 1 in the possession or control of the associated patient (or a designated, authorized surrogate such as a nurse, a family member, a law enforcement officer, a substance abuse counselor, an aide, etc.)—for simplicity purposes, the user will be referred to generally herein as "patient." In at least one embodiment, and as discussed further below, the at least one pill storage container 12 is controlled remotely by the associated at least one patient device 1. In at least one embodiment, as discussed further below, the patient device 1 is also in selective communication with an at least one clinician device 8 in the possession or control of a participating clinician tasked with monitoring the patient's proper consumption of the pills 14. It should be noted that, in at least one embodiment, the term "clinician" is intended to generally include any type of medical professional or medical entity which might be tasked with monitoring the patient's proper consumption of the pills 14—including but not limited to a physician, a nurse, a pharmacist, and an electronic medical record system.

At the outset, it should also be noted that the respective communication between each of the at least one tamper-proof pill storage container 12, at least one patient device 1, and at least one clinician device 8 may be achieved using any wired- or wireless-based communication protocol (or combination of protocols) now known or later developed. As such, the present invention should not be read as being limited to any one particular type of communication protocol, even though certain exemplary protocols may be mentioned herein for illustrative purposes. It should also be noted that the terms "patient device" and "clinician device" are intended to include any type of computing or electronic device, now known or later developed, capable of communicating with one another as described herein—such as desktop computers, mobile phones, smartphones, laptop computers, tablet computers, personal data assistants, gaming devices, wearable devices, etc. As such, the system 20 should not be read as being limited to use with any one particular type of computing or electronic device, even though certain exemplary devices may be mentioned or shown herein for illustrative purposes.

Figure 2:
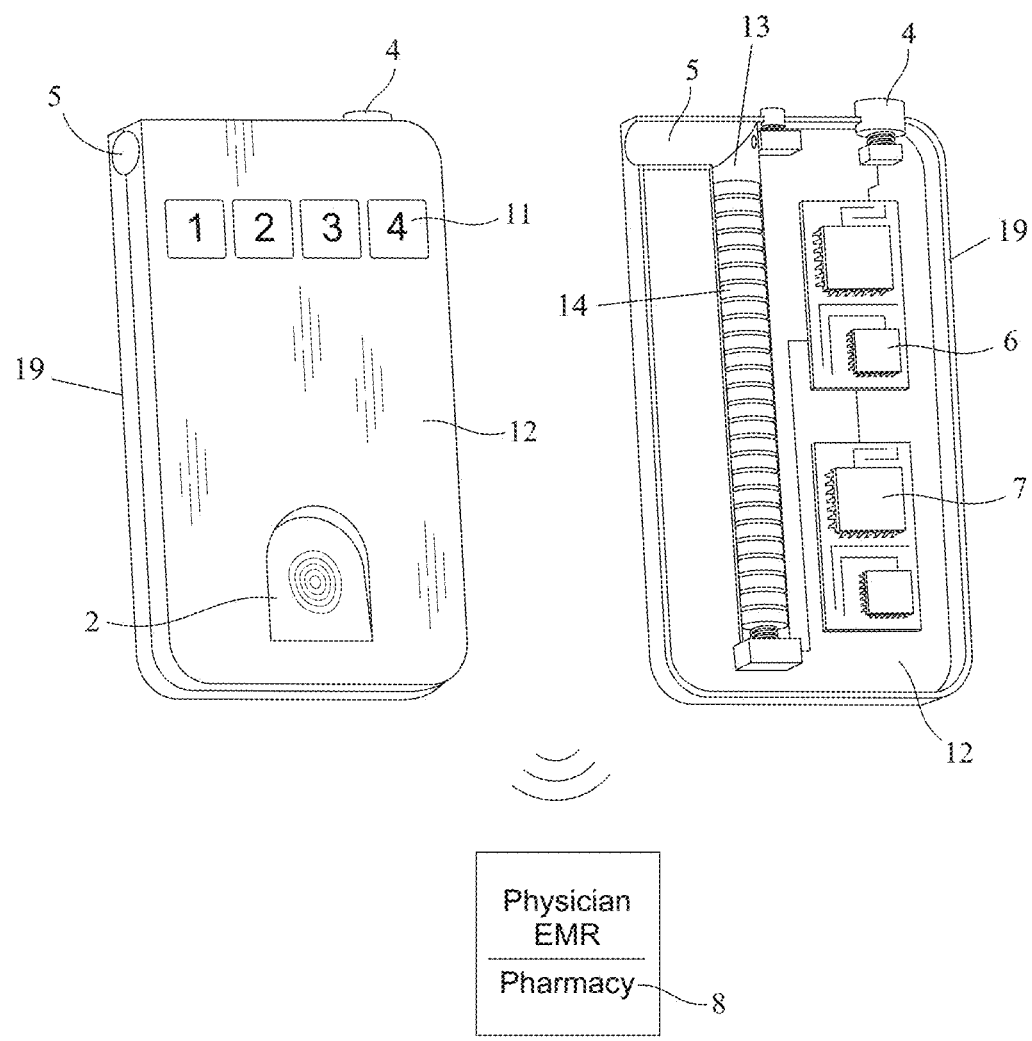
FIG. 2 is a simplified schematic view of a further exemplary tamper-proof pill dispensing system, in accordance with at least one embodiment.

With continued reference to FIG. 1, in the exemplary embodiment, each of the at least one tamper-proof pill storage container 12, at least one patient device 1, and at least one clinician device 8 contains the hardware and software necessary to carry out the exemplary methods for administering the pill dispensing system 20, as described herein. In at least one embodiment, the at least one patient device 1 provides a patient application 3 residing locally in memory 9 on the patient device 1, the patient application 3 being configured for selectively communicating with at least one of the at least one pill storage container 12 and the at least one clinician device 8, as discussed further below. It should be noted that the term "memory" is intended to include any type of electronic storage medium (or combination of storage mediums) now known or later developed, such as local hard drives, RAM, flash memory, secure digital ("SD") cards, external storage devices, network or cloud storage devices, integrated circuits, etc. Additionally, the various components of each of the at least one patient device 1 and clinician device 8 may reside on a single computing and/or electronic device, or may separately reside on two or more computing and/or electronic devices in communication with one another. In at least one alternate embodiment, the functionality provided by the patient application 3 resides remotely in memory on the at least one clinician device 8 (or a server in communication with the at least one clinician device 8—hereinafter collectively referred to as the clinician device 8 for simplicity purposes), with the at least one patient device 1 capable of accessing said functionality via an online portal hosted by the clinician device 8 and/or server, either in addition to or in lieu of the patient application 3 residing locally in memory 9 on the at least one patient device 1. It should be noted that, for simplicity purposes, the functionality provided by the patient application 3 will be described herein as such—even though certain embodiments may provide some or all of said functionality through an online portal. It should also be noted that, for simplicity purposes, when discussing functionality and the various methods that may be carried out by the system 20 herein, the terms "patient device" and "patient application" are intended to be interchangeable. In at least one embodiment, the at least one patient device 1 provides an at least one display screen 10 for providing an at least one graphical user interface to allow the associated patient to access and utilize the various functions provided by the system 20. Additionally, in at least one embodiment, the at least one patient device 1 provides an at least one biometric sensor 2, the purpose of which is discussed further below. In at least one such embodiment, the at least one biometric sensor 2 is at least one of a fingerprint scanner, a facial recognition system (i.e., a camera with corresponding facial recognition software), an iris scanner, and a retinal scanner. In still further embodiments, the at least one biometric sensor 2 may be any other type of biometric sensor now known or later developed. In at least one alternate embodiment, as illustrated in FIG. 2, the at least one pill storage container 12 provides the at least one biometric sensor 2. In at least one embodiment, as also illustrated in FIG. 2, the at least one pill storage container 12 further provides a combination lock 11. In at least one alternate embodiment, the combination lock functionality is implemented electronically by the patient application 3 via the display screen 10 of the patient device 1.

FIG. 1 also illustrates the internal components contained within a housing 19 of the at least one pill storage container 12, in at least one embodiment. In that regard, it should be noted that the particular size, shape and dimensions of the housing 19 shown in the drawings is merely exemplary and is being shown for illustrative purposes. In further embodiments, the housing 19 may take on any other size, shape or dimensions now known or later conceived—for example, a square or rectangular box, an oval container, an oblong container, a cylindrical container, or a pen-shaped container. With continued reference to FIG. 1, in at least one embodiment, the pill storage container 12 provides an at least one pill magazine 13 positioned within the housing 19 and configured for storing and selectively dispensing a plurality of pills 14 through a pill outlet 5 provided by the housing 19. In at least one embodiment, the pill magazine 13 is spring-loaded. In at least one alternate embodiment, as illustrated in FIGS. 4A-4D, the pill magazine 13 is in mechanical communication with a drive shaft 16 positioned and configured for ejecting a pill 14 from the pill magazine 13 through the pill outlet 5. In at least one such embodiment, an at least one battery 17 is in electrical communication with a solenoid 18, and a magazine drive shaft 15 is in operable connection with the drive shaft 16, which in turn is in operable connection with the solenoid 18. In still further embodiments, the pill storage container 12 may provide any other mechanism or combination of mechanisms, now known or later developed, capable of ejecting a pill 14 from the pill magazine 13 through the pill outlet 5.

In at least one embodiment, as illustrated in FIGS. 7A-7C and 8A-8C, the housing 19 further provides a selectively lockable outlet cover 22 positioned and configured for selectively restricting access to the pill outlet 5, as discussed further below. In at least one embodiment, as best illustrated in FIG. 1, the housing 19 further provides an actuator 4 configured for causing a pill 14 to be ejected from the pill magazine 13 through the pill outlet 5. In at least one such embodiment, the actuator 4 is a button. However, in alternate embodiments, the actuator 4 may be any other mechanism or combination of mechanisms, now known or later developed, capable of mechanically or electrically causing a pill 14 to be ejected from the pill magazine 13 through the pill outlet 5. In at least one embodiment, the housing 19 further provides a wireless microcontroller 6 and a power source 7. In at least one such embodiment, the power source 7 is at least one of an internal battery, an external battery, and an AC/DC electrical plug.

In at least one embodiment, the pill storage container 12 provides an at least one tamper-proof substance positioned and configured for selectively rendering the pills 14 inert, inactive or intolerable to the patient in the event the pill storage container 12 or the pill magazine 13 is tampered with. In at least one such embodiment, the tamper-proof substance is cyanoacrylate configured for being released and coating the pills 14 in the event the housing 19 of the pill storage container 12 or the pill magazine 13 is physically compromised—i.e., if an attempt is made to access the pills 14 in any way, when access to the pills 14 is otherwise not permitted. In at least one embodiment, the cyanoacrylate is at least one of methyl cyanoacrylate, ethyl cyanoacrylate, N-butyl cyanoacrylate and 2-octyl cyanoacrylate. In another embodiment, the tamper-proof substance is methyl methacrylate configured for being released and coating the pills 14 in a gel in the event the housing 19 of the pill storage container 12 or the pill magazine 13 is physically compromised or exposed to water.

Figure 3:
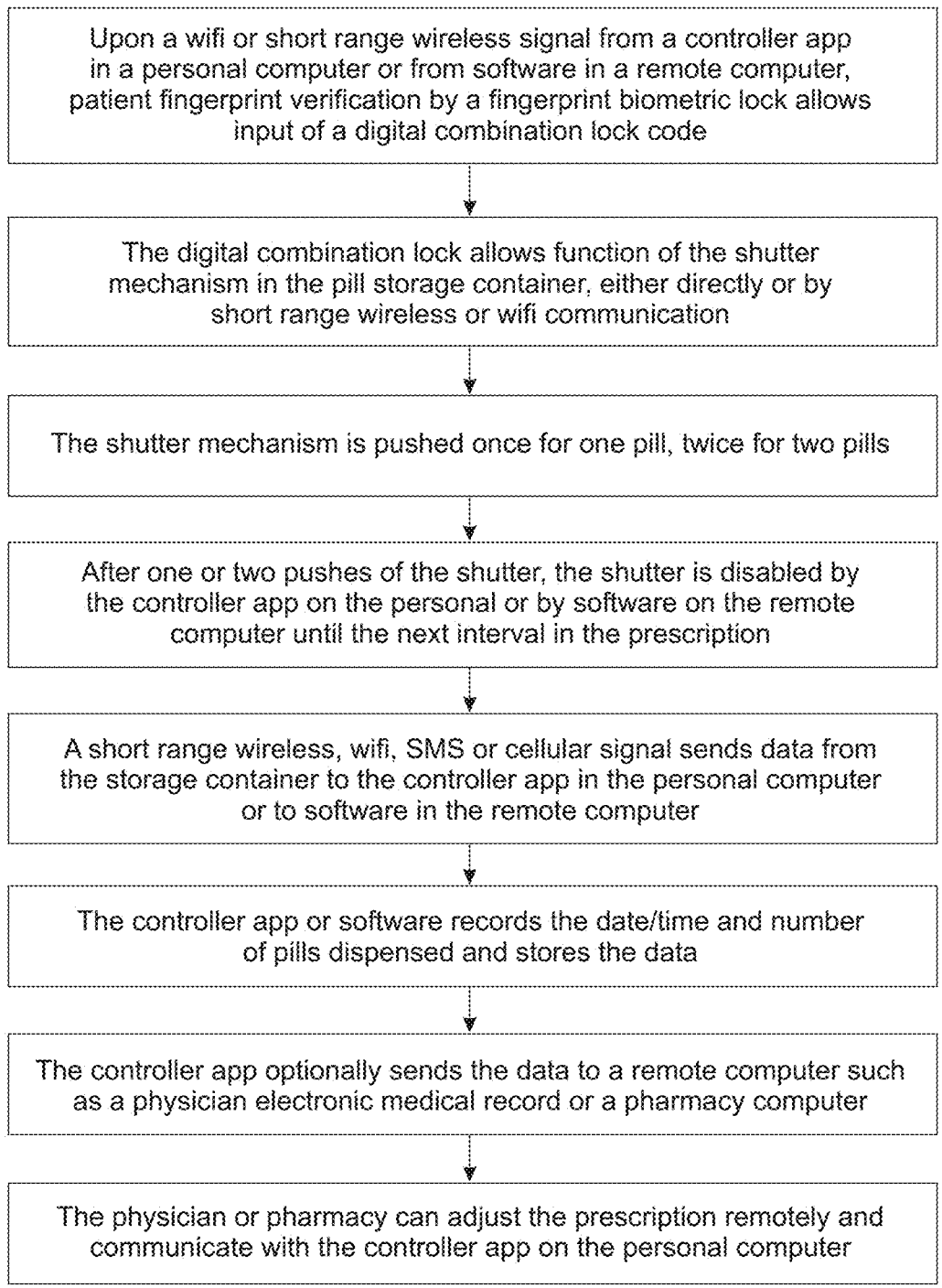
FIG. 3 is a flow diagram of an exemplary method for dispensing pills using the exemplary tamper-proof pill dispensing system, in accordance with at least one embodiment.
Figure 4A:
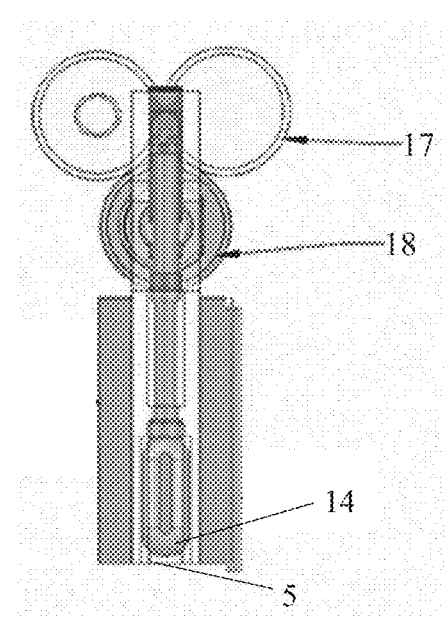
FIG. 4A is a cross-sectional view of a further exemplary pill storage container, in accordance with at least one embodiment.
Figure 4B:
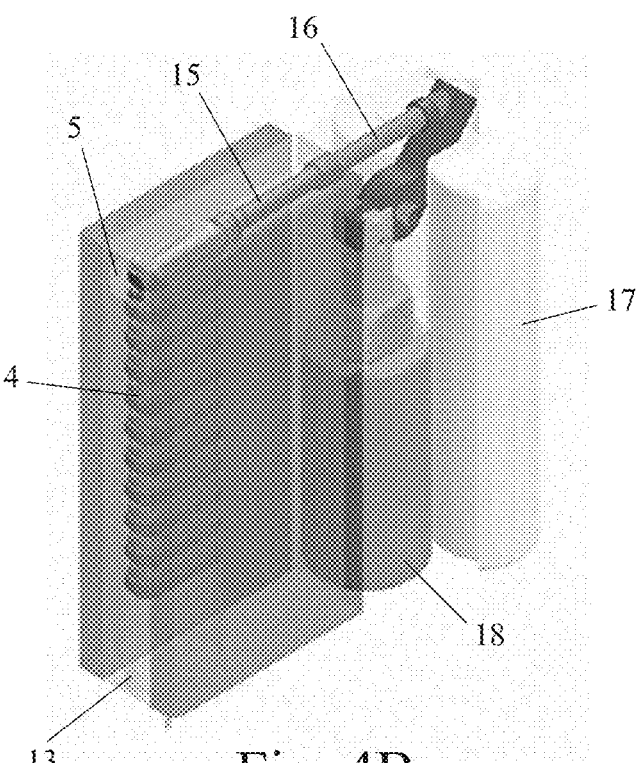
FIG. 4B is a perspective view of the pill storage container of FIG. 4A.
Figure 4C:
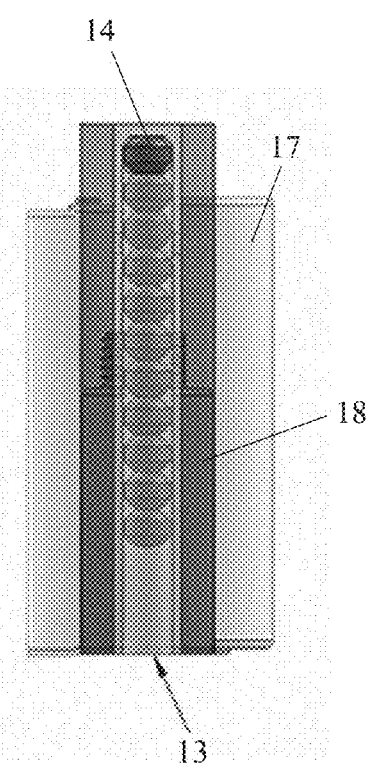
FIG. 4C is a cross-sectional view of a pill magazine of the pill storage container of FIG. 4A.
Figure 4D:
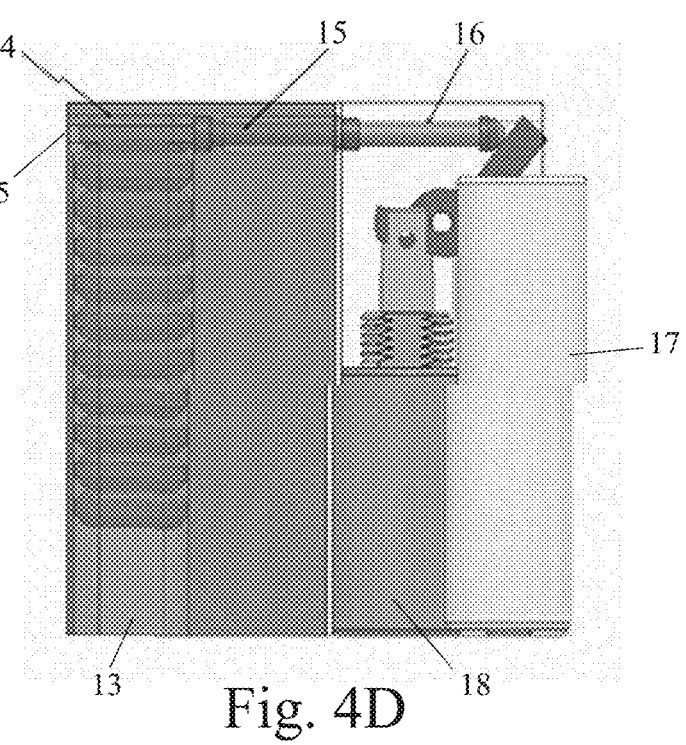
FIG. 4D is a side view of the pill storage container of FIG. 4A.
Figure 5A:
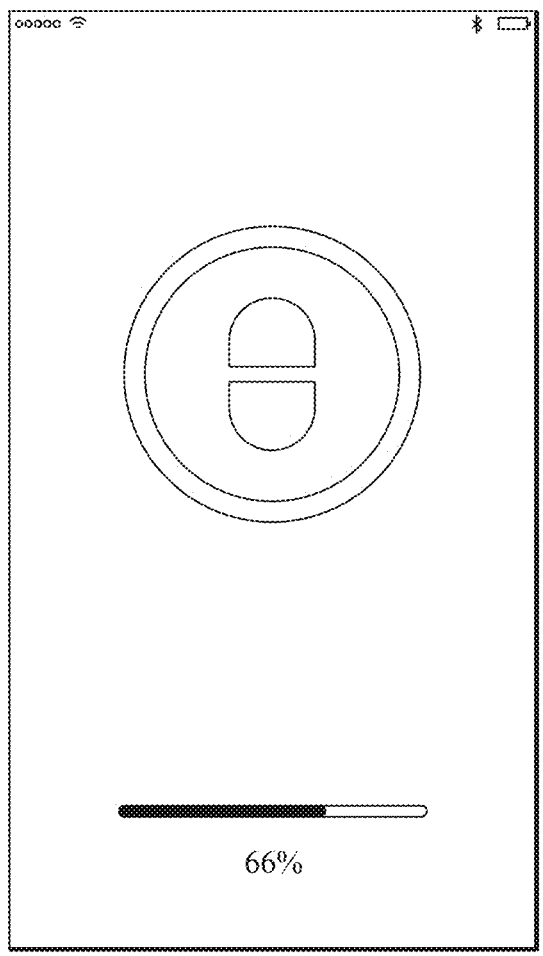
FIGS. 5A-5O are illustrations of exemplary user interfaces as displayed by an exemplary patient device, in accordance with at least one embodiment.
Figure 5B:
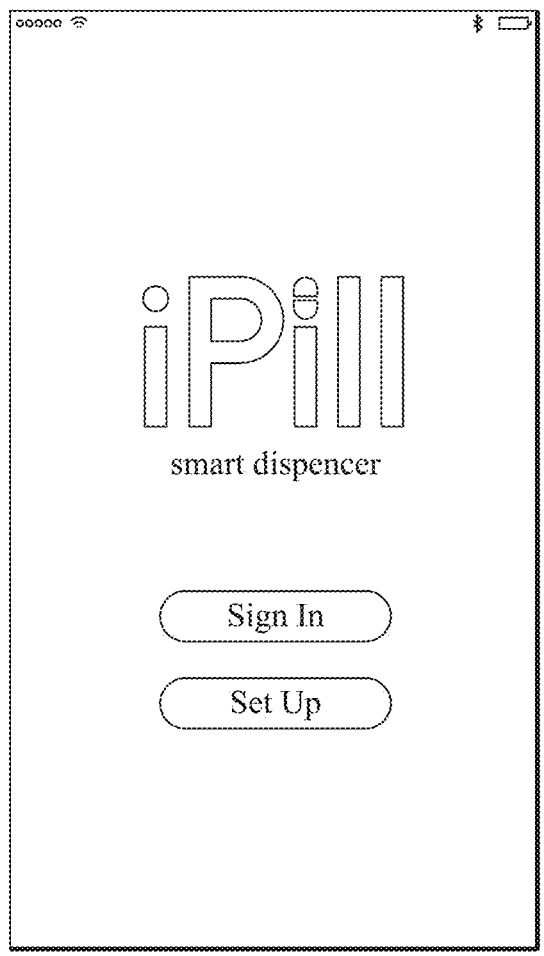
Figure 5C:
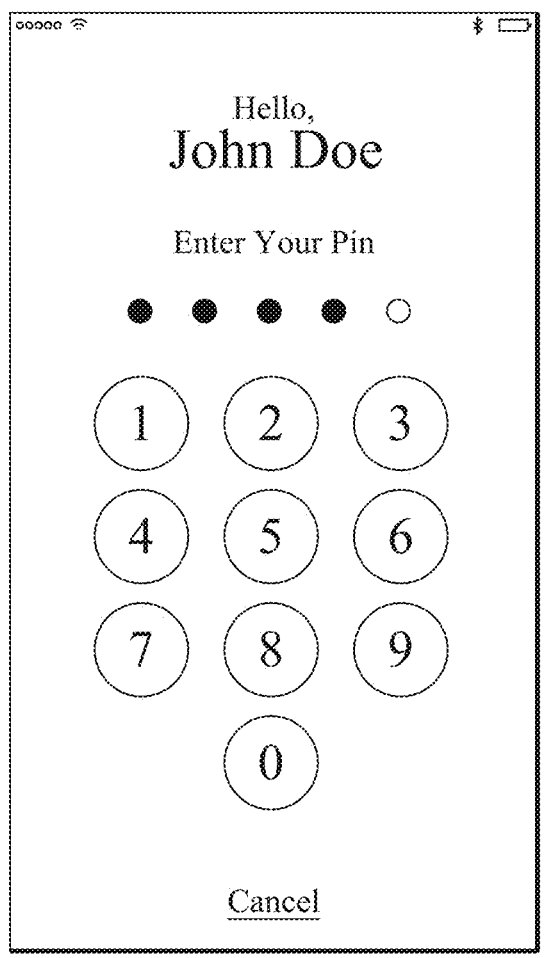
Figure 5D:
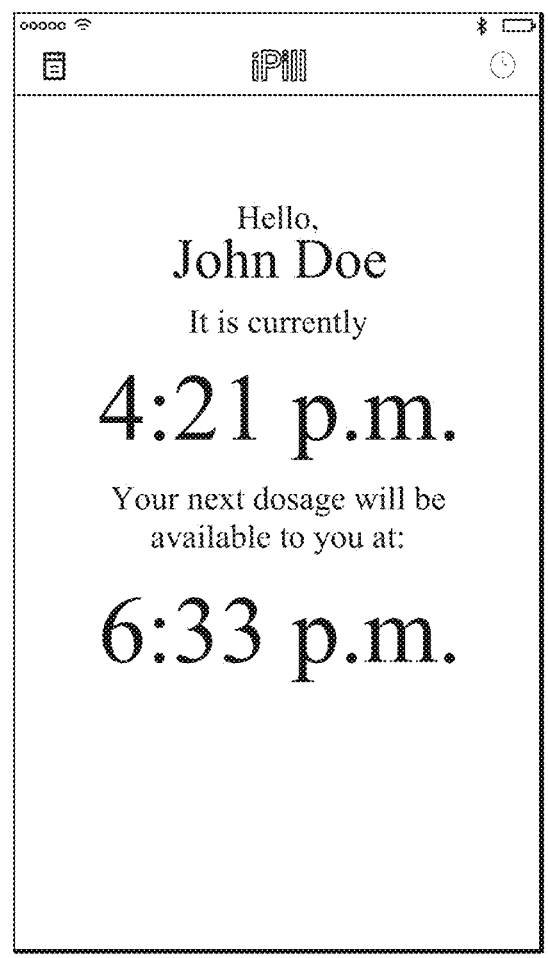
Figure 5E:
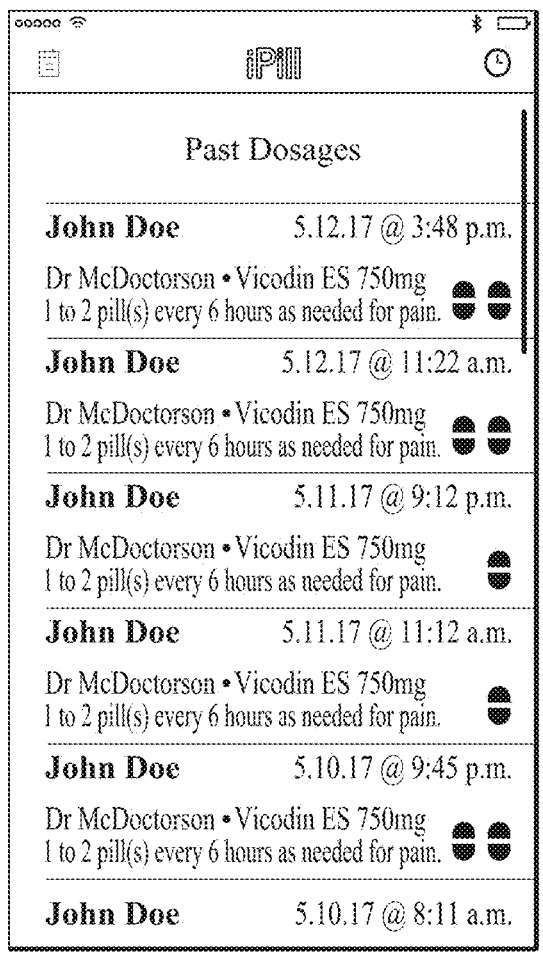
Figure 5F:
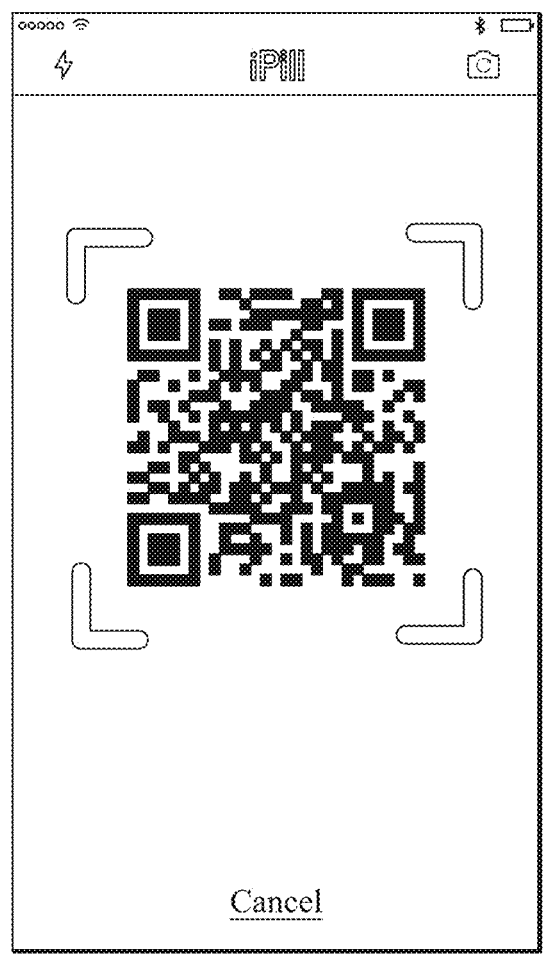
Figure 5G:
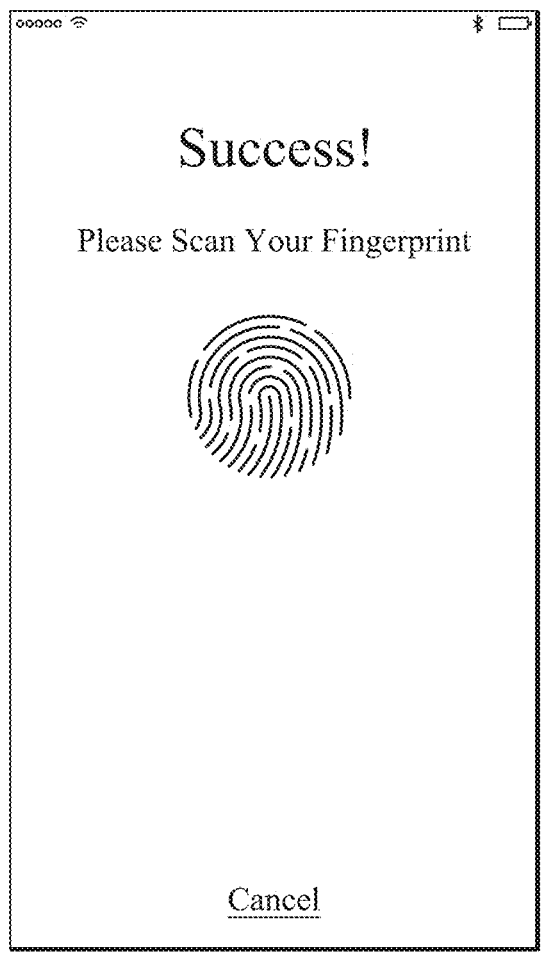
Figure 5H:
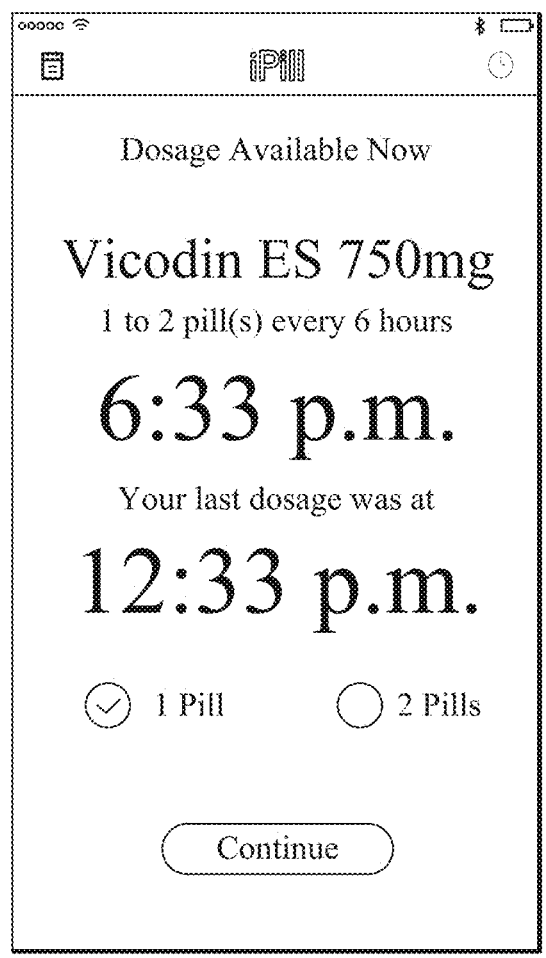
Figure 5I:
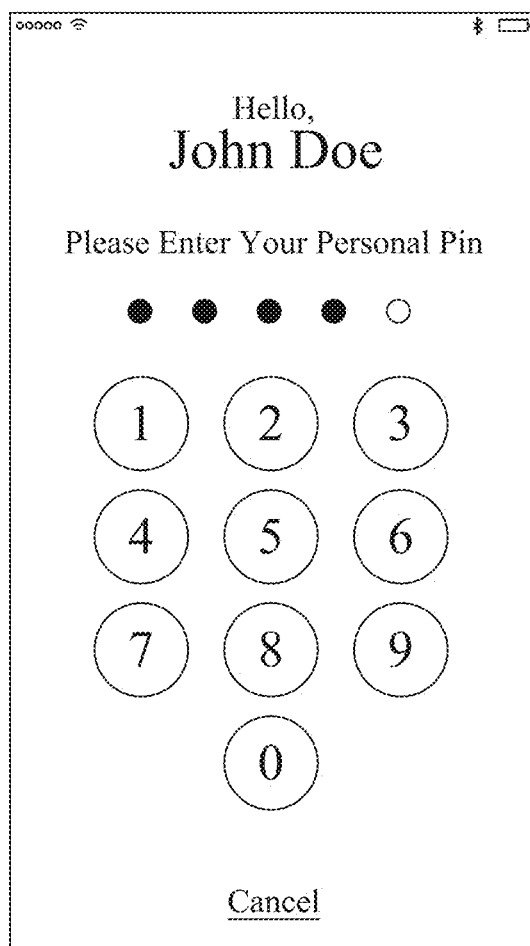
Figure 5J:
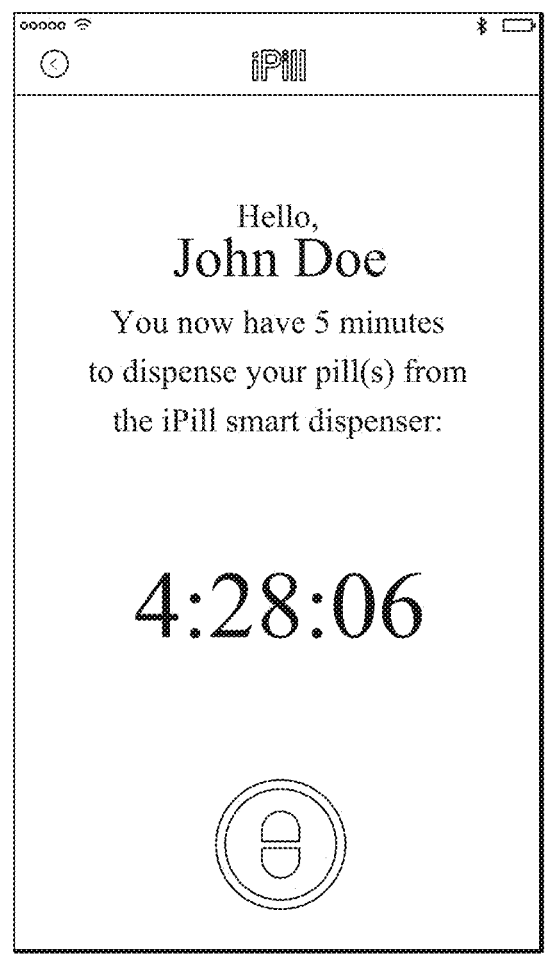
Figure 5K:
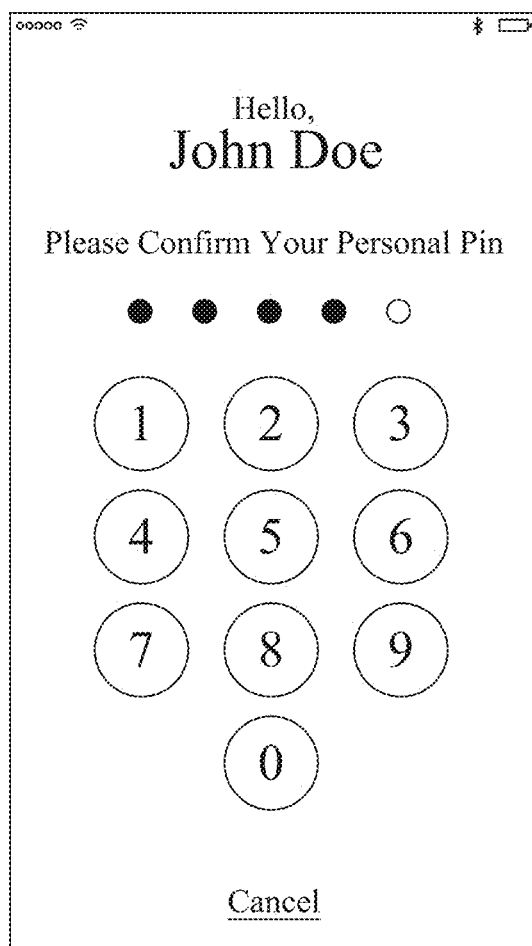
Figure 5L:
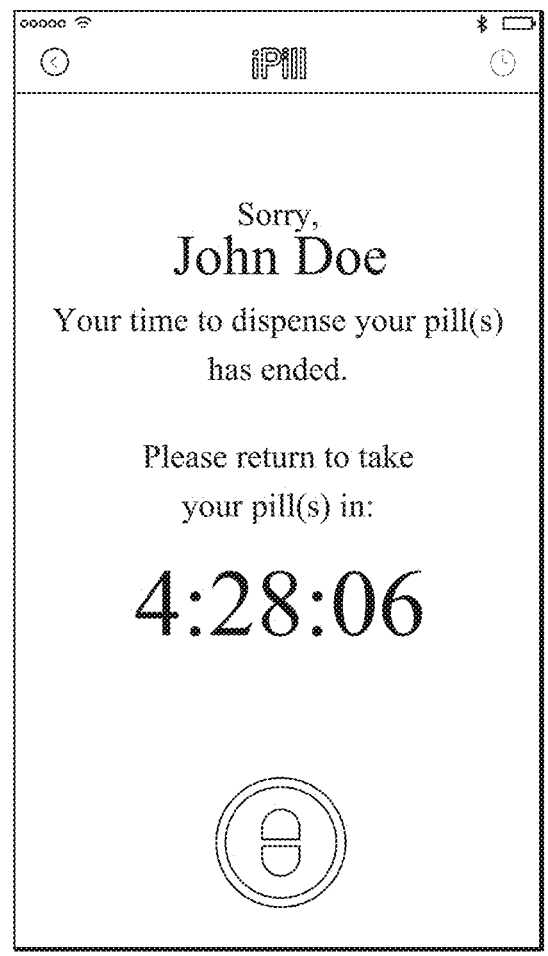
Figure 5O:
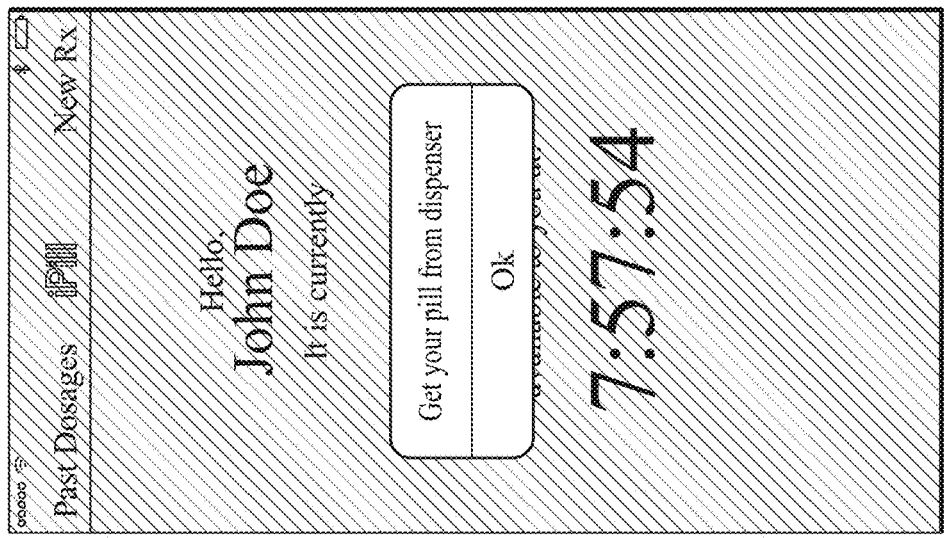
Figure 5N:
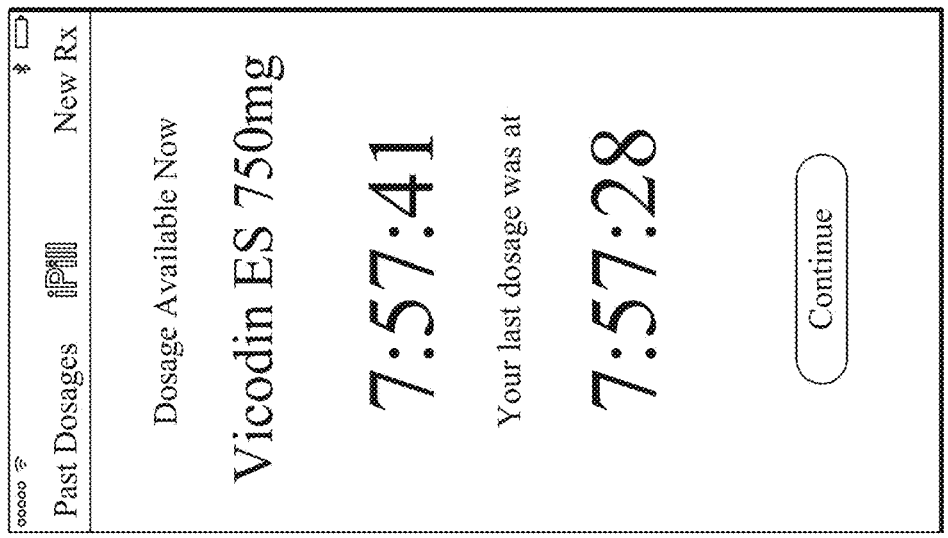
Figure 5M:
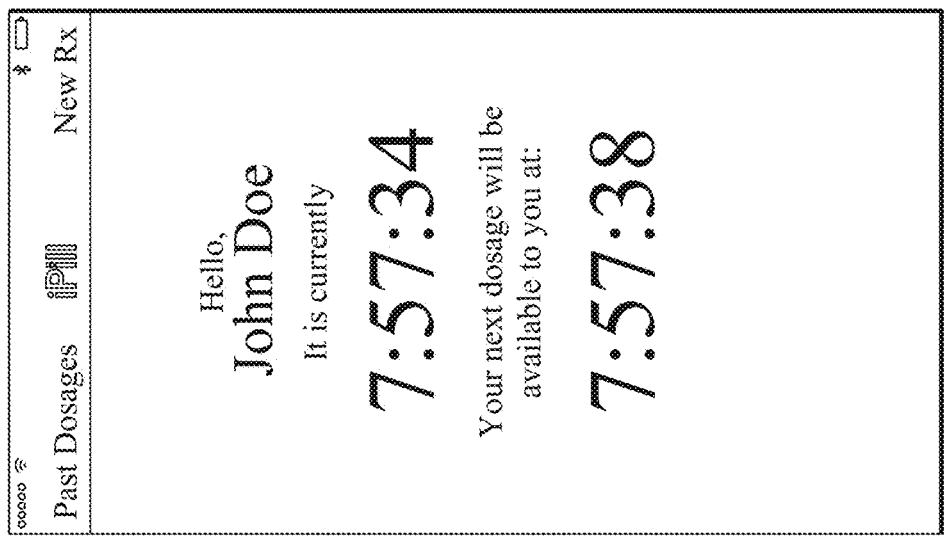
Figure 6A:
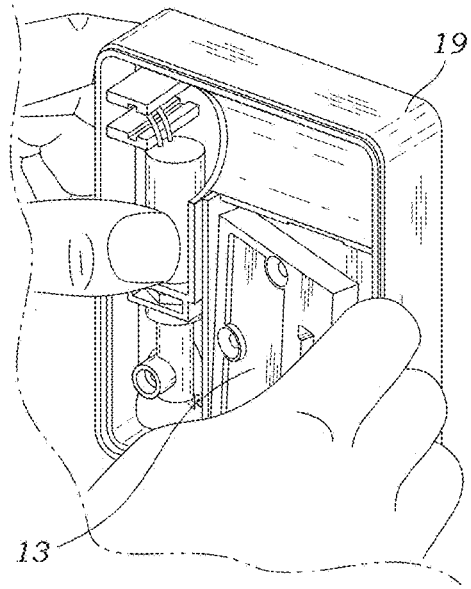
FIGS. 6A-6D are images of a further exemplary pill storage container, illustrating the sequential process of replacing an exemplary pill magazine, in accordance with at least one embodiment.
Figure 6B:
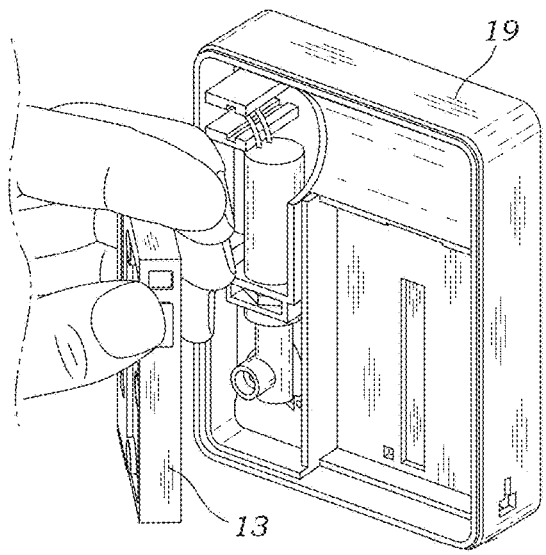
Figure 6C:
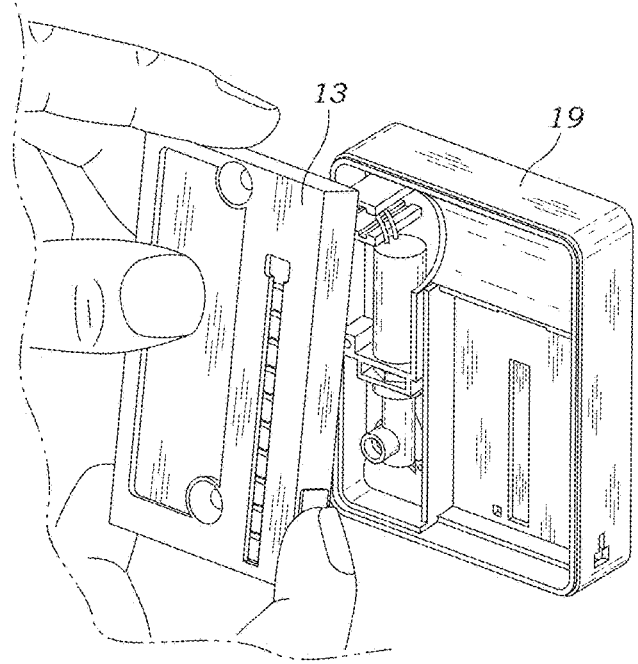
Figure 6D:
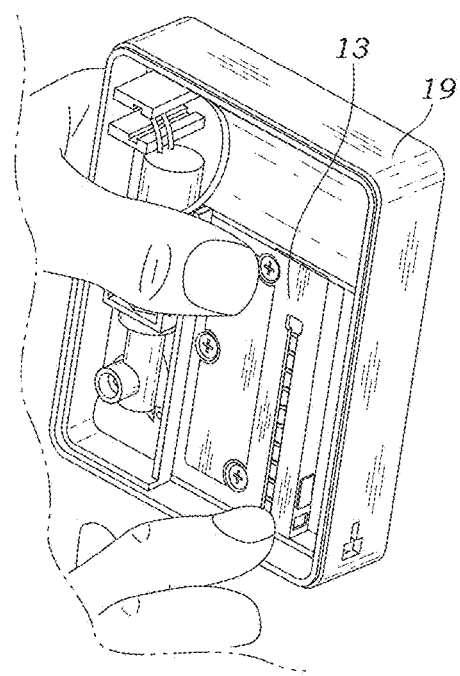
Figure 7C:
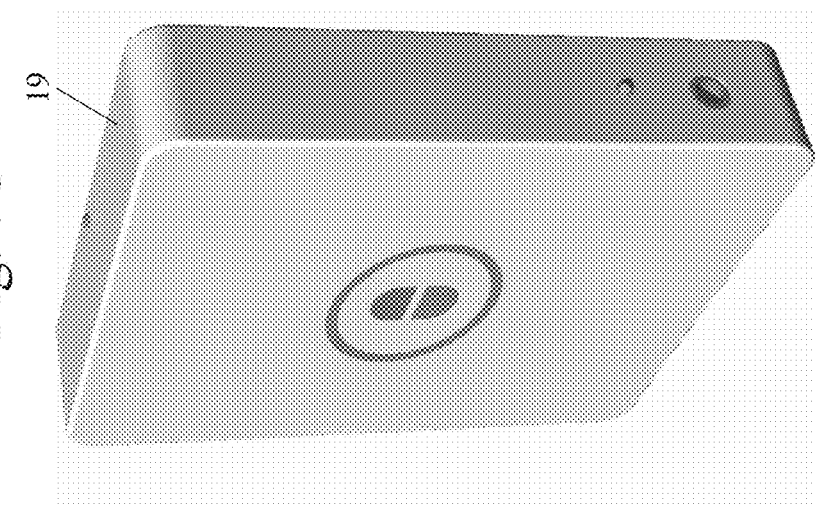
FIGS. 7A-7C are images of a still further exemplary pill storage container, in accordance with at least one embodiment.
Figure 7B:
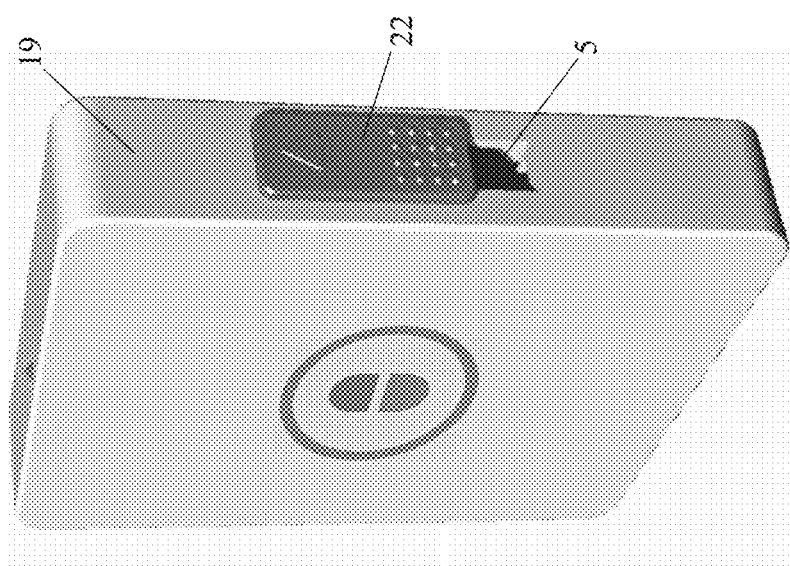
Figure 7A:
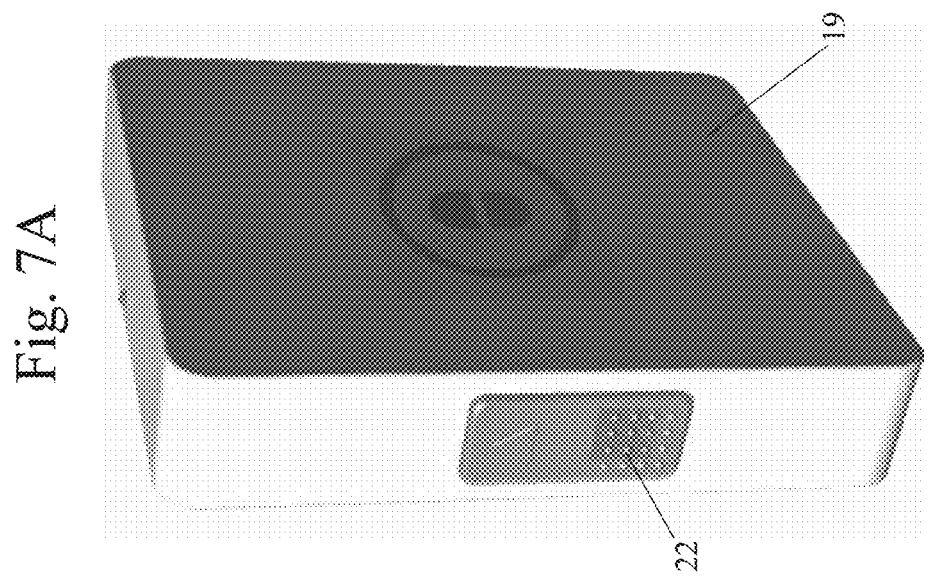

In at least one embodiment, as illustrated in the flow diagram of FIG. 3 as well as the exemplary user interfaces of FIGS. 5A-5O, through the patient application 3 residing either locally in memory 9 on the at least one patient device 1 or remotely on the clinician device 8, upon the associated patient utilizing the system 20 to manage the distribution of their prescribed pills 14, the patient application 3 first determines whether the associated patient is new to the system 20. If the associated patient is new, the patient is required to properly register a new user account with the system 20 via the patient application 3—or, alternatively, via any other computing or electronic device capable of communicating with the system 20. As part of the registration process, the patient is asked to provide select details related to at least one of the patient's personal information, as well as a security code and an at least one biometric marker associated with the patient (such as a fingerprint, a facial image, a retinal image, or an iris image for example). In at least one embodiment, the patient is also provided with the at least one pill storage container 12, which is then associated with the patient device 1 for enabling selective communication therebetween, as discussed further below. In at least one embodiment, the pills 14 are loaded into the pill storage container 12 (via the pill magazine 13) by an authorized clinician, to better ensure that the patient will not attempt to misuse or share the pills 14. If the pills 14 are associated with a new prescription, the patient application 3 requires the patient (or the clinician) to register the prescription with the patient application 3. In at least one such embodiment, the patient is able to register the prescription by scanning or inputting a unique prescription code into the patient application 3, with the prescription code containing the necessary information related to the prescription distribution, including a dosage interval (i.e., the amount of time between distributing the pills 14) and a dosage quantity (i.e., the quantity of pills 14 to be distributed at each dosage interval). In at least one such embodiment, the patient is able to register the prescription by scanning a visual barcode (such as a QR code, for example) using a camera 24 of the patient device 1. In at least one embodiment, the patient application 3 encrypts each of the biometric marker, security code and prescription code with a unique hash value (such as a random number, in at least one embodiment) to be stored in each of the patient device 1 and the associated pill storage container 12, thereby creating a unique link therebetween. In this way, only the associated patient device 1 is capable of transmitting instructions to the pill storage container 12, with the associated patient device 1 itself only being accessible by the associated patient, based on the patient's unique biometric marker and security code, which better prevents anyone else from accessing the pills 14.

In at least one embodiment, after the prescription has been registered with the patient application 3, the patient application 3 provides a countdown timer or otherwise notes the date and time for the next dosage (based on the associated dosage interval) via the display screen 10 of the patient device 1. Upon determining that the next dosage is available for the patient, the patient application 3 notifies the patient using at least one of an audible, visual and/or vibrational alert via the patient device 1. In at least one embodiment, the patient is required to provide the appropriate biometric marker via the at least one biometric sensor 2 and also input their security code via either the patient application 3 or a combination lock 11 provided by the pill storage container 12. In at least one such embodiment, the patient must provide the appropriate biometric marker within a finite, pre-defined period of time—such as within five minutes from the patient application 3 notifying the patient of the dosage availability, for example—else the pills 14 will not be distributed to the patient for that dosage interval. Additionally, in at least one such embodiment, the patient must input their security code within a finite, pre-defined period of time—such as within one minute from the patient providing the appropriate biometric marker, for example—else the pills 14 will not be distributed to the patient for that dosage interval. Additionally, in at least one such embodiment, the patient application 3 requires the patient to provide the appropriate biometric marker and the security code in sequence. Upon the patient application 3 authenticating the provided biometric marker and security code, the patient application 3 transmits a signal to the pill storage container 12, instructing the pill storage container 12 to distribute a quantity of pills 14 equal to the associated dosage quantity via the pill outlet 5. In at least one embodiment, the pill storage container 12 will only distribute the quantity of pills 14 after the patient activates the actuator 4 positioned on the housing 19 of the pill storage container 12. In at least one embodiment, where the housing 19 of the pill storage container 12 provides a selectively lockable outlet cover 22 positioned and configured for selectively restricting access to the pill outlet 5, the outlet cover 22 is temporarily unlocked to allow the patient access to the pill outlet 5. In at least one such embodiment, the actuator 4 must be activated by the patient within a finite, pre-defined period of time—such as within five minutes from the patient application 3 notifying the patient of the dosage availability, for example—else the pills 14 will not be distributed to the patient for that dosage interval. Upon the pill storage container 12 distributing the pills to the patient, the pill storage container 12 transmits a signal back to the patient application 3, and the patient application 3 schedules the next dosage based on the associated dosage interval. In at least one embodiment, the patient application 3 also records the date, time and dosage quantity, which can be subsequently reviewed by the patient or an authorized clinician. In at least one such embodiment, the patient application 3 utilizes blockchain to securely store this data, so as to maintain a tamper-proof record that may be reviewed by the authorized clinician. In at least one embodiment, if the patient attempts to obtain pills 14 during any time other than the scheduled dosage times, the patient application 3 informs the patient that they must wait until the next scheduled dosage time.

In at least one embodiment, the patient device 1, via the patient application 3, can also securely transmit the data to the at least one clinician device 8. In at least one embodiment, an authorized user of the clinician device 8 can change the patient's prescription—including the associated dosage interval and dosage quantity—and communicate the changes to the patient application 3. In at least one embodiment, the clinician device 8 is capable of securely transmitting other messages to the patient application 3 as well.

In at least one embodiment, upon the patient application 3 determining that the at least one pill magazine 13 of the pill storage container 12 is empty or running low, the patient application 3 notifies the patient that a new prescription (or alternatively, a refill) is required. In at least one such embodiment, where the patient application 3 is in selective communication with the at least one clinician device 8, the patient application 3 also notifies the associated clinician that a new prescription (or alternatively, a refill) is required. The process of removing the empty pill magazine 13 from the pill storage container 12 and inserting a full pill magazine 13, in accordance with at least one embodiment, is sequentially illustrated in FIGS. 6A-6D.

Figure 9:
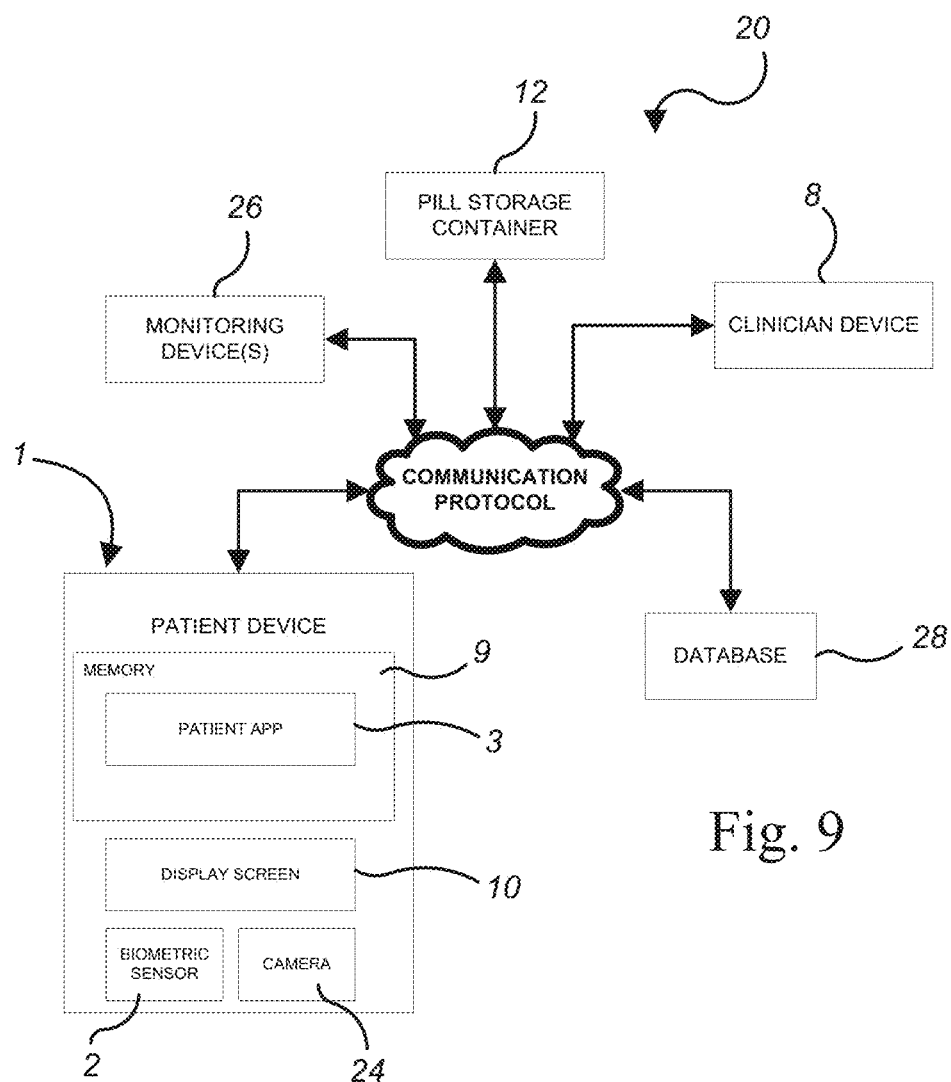
FIG. 9 is a simplified schematic view of a further exemplary tamper-proof pill dispensing system, in accordance with at least one embodiment.
Figure 10:
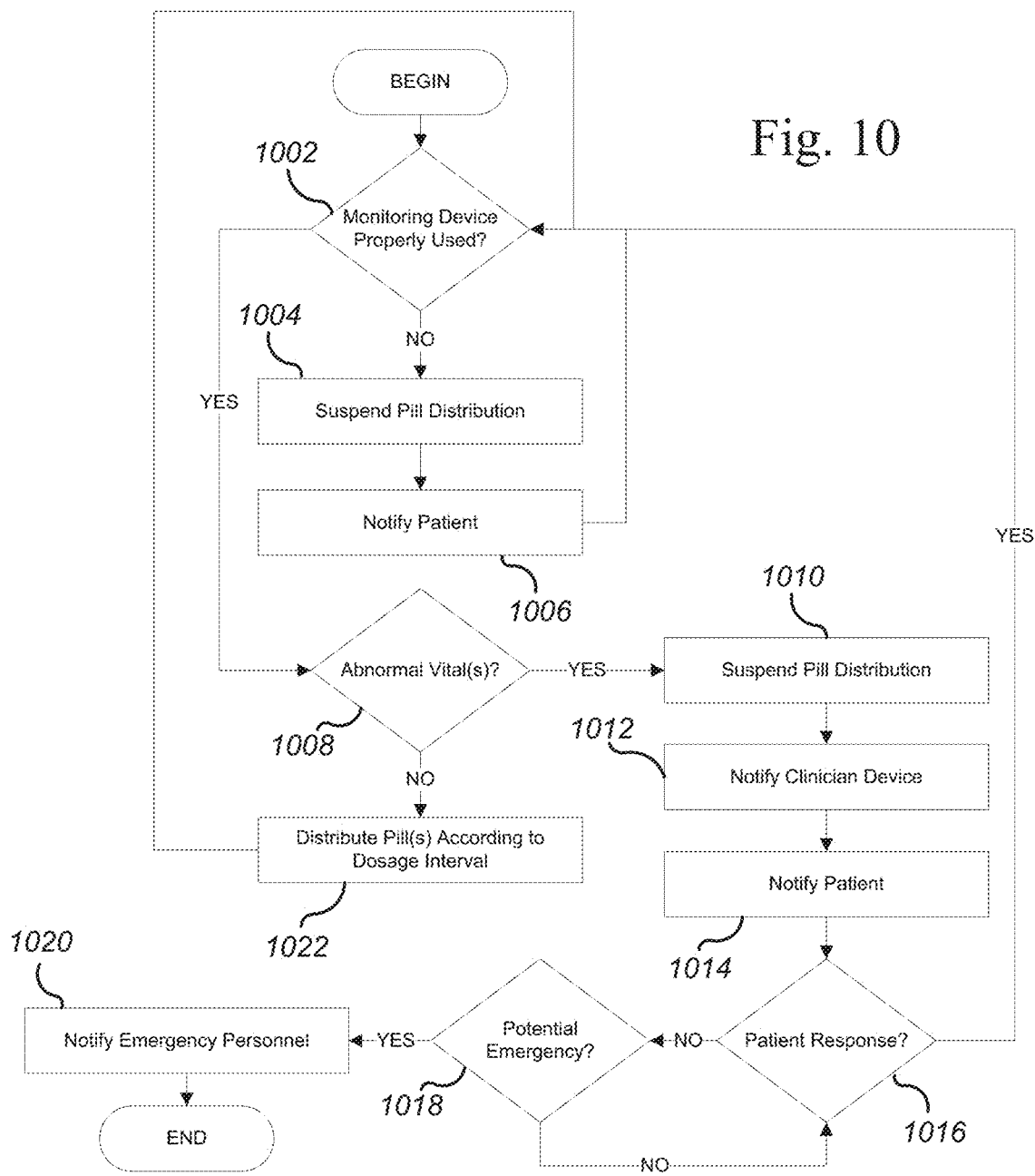
FIG. 10 is a flow diagram of a further exemplary method for dispensing pills using the exemplary tamper-proof pill dispensing system, in accordance with at least one embodiment.

In at least one embodiment, as illustrated in the simplified schematic view of FIG. 9, the system 20 also provides an at least one monitoring device 26 in selective communication with the patient device 1 and configured for assisting the patient application 3 with monitoring one or more vitals associated with the patient, in order to better manage the distribution of pills 14 to the patient. In at least one such embodiment, the at least one monitoring device 26 is a respiratory monitor positioned and configured for assisting the patient application 3 with monitoring a breathing rate of the patient, utilizing acoustic respiratory monitoring or impedance respiratory monitoring for example. In further embodiments, the at least one monitoring device 26 may include any other type of device, sensor, or combination thereof—now known or later developed—capable of substantially carrying out the functionality described herein. In at least one embodiment, the patient device 1 and the at least one monitoring device 26 are one and the same—as such, it is intended that those terms as used herein are to be interchangeable with one another. In at least one embodiment, as illustrated in the flow diagram of FIG. 10, upon the patient application 3 determining that the at least one monitored vital falls below or rises above a pre-defined vital threshold (1008)—i.e., if the at least one monitored vital is determined to be abnormal—the patient application 3 attempts to notify the patient using at least one of an audible, visual and/or vibrational alert via the patient device 1 (1014). In at least one embodiment, the patient application 3 will also transmit a notification to the at least one associated clinician device 8 (1012). Additionally, in at least one embodiment, if the patient fails to timely respond to the notification via the patient application 3 (1016), depending on the degree of abnormality in the at least one monitored vital (1018)—for example, where the patient application 3 determines that the patient is not breathing—the patient application 3 automatically alerts local emergency personnel and provides the patient's current location based on the GPS location of the patient device 1 (1020). Additionally, in at least one embodiment, upon the patient application 3 determining that the at least one monitored vital is abnormal (1008), the patient application 3 may temporarily suspend future distributions of the pills 14 (1010) until the at least one monitored vital returns to normal. In this way, the patient application 3 is able to monitor the effects of the pills 14 and automatically respond accordingly. Similarly, in at least one embodiment, upon the patient application 3 determining that the patient is not properly using the at least one monitoring device 26 (1002)—for example, if the user is not wearing the at least one monitoring device 26 in the proper position, or not wearing the at least one monitoring device 26 at all—the patient application 3 attempts to notify the patient using at least one of an audible, visual and/or vibrational alert via the patient device 1 (1006) and may also temporarily suspend future distributions of the pills 14 (1004) until the patient begins using the at least one monitoring device 26 properly.

In at least one embodiment, the system 20 further provides an at least one database 28 in selective communication with the patient device 1 and configured for storing data obtained by each of the patient application 3 and the at least one monitoring device 26, as discussed above. In at least one embodiment, the patient device 1 and database 28 are one and the same—as such, it is intended that those terms as used herein are to be interchangeable with one another as well.

Aspects of the present specification may also be described as follows:

1. A method for administering a pill dispensing system for managing the distribution of pills to a patient, the method comprising the steps of: implementing an at least one tamper-proof pill storage container that provides an at least one pill magazine positioned within a housing of the pill storage container and configured for storing and selectively dispensing a plurality of pills through a pill outlet provided by the housing; implementing a patient application residing in memory on an at least one patient device under the control of the patient, the patient application in selective communication with the at least one pill storage container; implementing an at least one monitoring device in selective communication with the patient application, the at least one monitoring device configured for assisting the patient application with monitoring an at least one vital of the patient; obtaining from the patient, via the patient application, a security code; obtaining from the patient, via an at least one biometric sensor provided by at least one of the at least one patient device and the at least one pill storage container, an at least one biometric marker associated with the patient; registering, via the patient application, a prescription associated with the pills contained within the at least one pill magazine of the at least one pill storage container, said prescription including a dosage interval and a dosage quantity; upon the patient application determining that a dosage of the pills is available for the patient, based on the associated dosage interval: notifying the patient via at least one of an audible alert, a visual alert and a vibrational alert via the at least one patient device; obtaining from the patient the security code; obtaining from the patient the at least one biometric marker; and upon the patient application authenticating the security code and the at least one biometric marker: transmitting a signal, via the patient application, to the at least one pill storage container, instructing said pill storage container to distribute a quantity of pills equal to the associated dosage quantity; and upon said pill storage container distributing the pills to the patient: transmitting a signal, via said pill storage container, back to the patient application; and scheduling, via the patient application, a future dosage of the pills based on the associated dosage interval; and upon the patient application determining that the at least one monitored vital is abnormal: notifying the patient via at least one of an audible alert, a visual alert and a vibrational alert via the at least one patient device; and temporarily suspending future dosages of the pills until the patient application determines that said monitored vital has returned to normal.

2. The method according to embodiment 1, wherein the step of obtaining an at least one biometric marker associated with the patient further comprises the step of obtaining at least one of a fingerprint of the patient, a facial image of the patient, a retinal image of the patient, and an iris image of the patient.

3. The method according to embodiments 1-2, wherein the step of registering a prescription associated with the pills further comprises the step of processing, via the patient application, a unique prescription code associated with the pills, said prescription code containing the dosage interval and the dosage quantity.

4. The method according to embodiments 1-3, wherein the step of processing a unique prescription code associated with the pills further comprises the step of scanning a visual barcode associated with the pills using a camera of the at least one patient device, said visual barcode containing the dosage interval and the dosage quantity.

5. The method according to embodiments 1-4, further comprising the step of encrypting, via the patient application, each of the biometric marker, security code and prescription code with a unique hash value to be stored in each of the at least one patient device and the associated at least one pill storage container, thereby establishing a unique link therebetween.

6. The method according to embodiments 1-5, wherein the step of instructing said pill storage container to distribute a quantity of pills equal to the associated dosage quantity further comprises the step of requiring the patient to activate an actuator positioned on the housing of said pill storage container in order for the pills to be distributed.

7. The method according to embodiments 1-6, further comprising the step of, upon said pill storage container distributing the pills to the patient, recording, via the patient application, a date, time and dosage quantity associated with the distributed pills.

8. The method according to embodiments 1-7, wherein the patient application is further in selective communication with an at least one clinician device under the control of a clinician tasked with monitoring the patient's proper consumption of the pills, the at least one clinician device capable of receiving data related to the distribution of pills to the patient, as well as transmitting dosage interval and dosage quantity changes to the patient application.

9. The method according to embodiments 1-8, wherein the step of the patient application determining that the at least one monitored vital is abnormal further comprises the step of notifying the at least one clinician device, via the patient application, of the abnormal vital.

10. The method according to embodiments 1-9, further comprising the step of, upon the patient application determining that the at least one pill magazine of the at least one pill storage container is empty or running low, automatically notifying at least one of the patient and clinician that a new prescription or refill is required.

11. The method according to embodiments 1-10, further comprising the step of, upon the at least one pill storage container being tampered with, automatically releasing an at least one tamper-proof substance within said pill storage container in order to render the pills inert, inactive or intolerable.

12. The method according to embodiments 1-11, wherein the step of releasing an at least one tamper-proof substance further comprises the step of releasing cyanoacrylate.

13. The method according to embodiments 1-12, wherein the step of releasing an at least one tamper-proof substance further comprises the step of releasing methyl methacrylate.

14. The method according to embodiments 1-13, wherein the step of implementing an at least one monitoring device further comprises the step of implementing an at least one respiratory monitor positioned and configured for obtaining a breathing rate of the patient.

15. The method according to embodiments 1-14, wherein the step of the patient application determining that the at least one monitored vital is abnormal further comprises the step of, upon the patient application failing to receive a response from the patient within a pre-defined period of time, automatically alerting, via the patient application, local emergency personnel.

16. The method according to embodiments 1-15, further comprising the step of, upon the patient application determining that the patient is not properly using the at least one monitoring device: notifying the patient via at least one of an audible alert, a visual alert and a vibrational alert via the at least one patient device; and temporarily suspending future dosages of the pills until the patient application determines that the patient is properly using the at least one monitoring device.

17. A method for administering a pill dispensing system for managing the distribution of pills to a patient, the method comprising the steps of: implementing an at least one tamper-proof pill storage container that provides an at least one pill magazine positioned within a housing of the pill storage container and configured for storing and selectively dispensing a plurality of pills through a pill outlet provided by the housing; implementing a patient application residing in memory on an at least one patient device under the control of the patient, the patient application in selective communication with the at least one pill storage container; implementing an at least one respiratory monitor in selective communication with the patient application, the at least one respiratory monitor configured for assisting the patient application with monitoring a breathing rate of the patient; obtaining from the patient, via the patient application, a security code; obtaining from the patient, via an at least one biometric sensor provided by at least one of the at least one patient device and the at least one pill storage container, an at least one biometric marker associated with the patient; registering, via the patient application, a prescription associated with the pills contained within the at least one pill magazine of the at least one pill storage container, said prescription including a dosage interval and a dosage quantity; upon the patient application determining that a dosage of the pills is available for the patient, based on the associated dosage interval: notifying the patient via at least one of an audible alert, a visual alert and a vibrational alert via the at least one patient device; obtaining from the patient the security code; obtaining from the patient the at least one biometric marker; and upon the patient application authenticating the security code and the at least one biometric marker: transmitting a signal, via the patient application, to the at least one pill storage container, instructing said pill storage container to distribute a quantity of pills equal to the associated dosage quantity; and upon said pill storage container distributing the pills to the patient: transmitting a signal, via said pill storage container, back to the patient application; and scheduling, via the patient application, a future dosage of the pills based on the associated dosage interval; and upon the patient application determining that the breathing rate of the patient is abnormal: notifying the patient via at least one of an audible alert, a visual alert and a vibrational alert via the at least one patient device; and temporarily suspending future dosages of the pills until the patient application determines that the breathing rate of the patient has returned to normal.

18. A pill dispensing system for managing the distribution of pills to a patient, the system comprising: an at least one tamper-proof pill storage container that provides an at least one pill magazine positioned within a housing of the pill storage container and configured for storing and selectively dispensing a plurality of pills through a pill outlet provided by the housing; a patient application residing in memory on an at least one patient device under the control of the patient, the patient application in selective communication with the at least one pill storage container; and an at least one monitoring device in selective communication with the patient application, the at least one monitoring device configured for assisting the patient application with monitoring an at least one vital of the patient; wherein, upon the patient desiring to utilize the system to manage the distribution of pills, the system is configured for: obtaining from the patient, via the patient application, a security code; obtaining from the patient, via an at least one biometric sensor provided by at least one of the at least one patient device and the at least one pill storage container, an at least one biometric marker associated with the patient; registering, via the patient application, a prescription associated with the pills contained within the at least one pill magazine of the at least one pill storage container, said prescription including a dosage interval and a dosage quantity; upon the patient application determining that a dosage of the pills is available for the patient, based on the associated dosage interval: notifying the patient via at least one of an audible alert, a visual alert and a vibrational alert via the at least one patient device; obtaining from the patient the security code; obtaining from the patient the at least one biometric marker; and upon the patient application authenticating the security code and the at least one biometric marker: transmitting a signal, via the patient application, to the at least one pill storage container, instructing said pill storage container to distribute a quantity of pills equal to the associated dosage quantity; and upon said pill storage container distributing the pills to the patient: transmitting a signal, via said pill storage container, back to the patient application; and scheduling, via the patient application, a future dosage of the pills based on the associated dosage interval; and upon the patient application determining that the at least one monitored vital is abnormal: notifying the patient via at least one of an audible alert, a visual alert and a vibrational alert via the at least one patient device; and temporarily suspending future dosages of the pills until the patient application determines that said monitored vital has returned to normal.

19. The pill dispensing system according to embodiment 18, wherein while obtaining an at least one biometric marker associated with the patient, the system is further configured for obtaining at least one of a fingerprint of the patient, a facial image of the patient, a retinal image of the patient, and an iris image of the patient.

20. The pill dispensing system according to embodiments 18-19, wherein while registering a prescription associated with the pills, the system is further configured for processing, via the patient application, a unique prescription code associated with the pills, said prescription code containing the dosage interval and the dosage quantity.

21. The pill dispensing system according to embodiments 18-20, wherein while processing a unique prescription code associated with the pills, the system is further configured for scanning a visual barcode associated with the pills using a camera of the at least one patient device, said visual barcode containing the dosage interval and the dosage quantity.

22. The pill dispensing system according to embodiments 18-21, wherein the system is further configured for encrypting, via the patient application, each of the biometric marker, security code and prescription code with a unique hash value to be stored in each of the at least one patient device and the associated at least one pill storage container, thereby establishing a unique link therebetween.

23. The pill dispensing system according to embodiments 18-22, wherein while instructing said pill storage container to distribute a quantity of pills equal to the associated dosage quantity, the system is further configured for requiring the patient to activate an actuator positioned on the housing of said pill storage container in order for the pills to be distributed.

24. The pill dispensing system according to embodiments 18-23, wherein upon said pill storage container distributing the pills to the patient, the system is further configured for recording, via the patient application, a date, time and dosage quantity associated with the distributed pills.

25. The pill dispensing system according to embodiments 18-24, wherein the patient application is further in selective communication with an at least one clinician device under the control of a clinician tasked with monitoring the patient's proper consumption of the pills, the at least one clinician device capable of receiving data related to the distribution of pills to the patient, as well as transmitting dosage interval and dosage quantity changes to the patient application.

26. The pill dispensing system according to embodiments 18-25, wherein while determining that the at least one monitored vital is abnormal, the system is further configured for notifying the at least one clinician device, via the patient application, of the abnormal vital.

27. The pill dispensing system according to embodiments 18-26, wherein upon the patient application determining that the at least one pill magazine of the at least one pill storage container is empty or running low, the system is further configured for automatically notifying at least one of the patient and clinician that a new prescription or refill is required.

28. The pill dispensing system according to embodiments 18-27, wherein upon the at least one pill storage container being tampered with, the system is further configured for automatically releasing an at least one tamper-proof substance within said pill storage container in order to render the pills inert, inactive or intolerable.

29. The pill dispensing system according to embodiments 18-28, wherein the at least one tamper-proof substance is cyanoacrylate.

30. The pill dispensing system according to embodiments 18-29, wherein the at least one tamper-proof substance is methyl methacrylate.

31. The pill dispensing system according to embodiments 18-30, wherein the at least one monitoring device is an at least one respiratory monitor positioned and configured for obtaining a breathing rate of the patient.

32. The pill dispensing system according to embodiments 18-31, wherein while determining that the at least one monitored vital is abnormal, the system is further configured for, upon the patient application failing to receive a response from the patient within a pre-defined period of time, automatically alerting, via the patient application, local emergency personnel.

33. The pill dispensing system according to embodiments 18-32, wherein the system if further configured for, upon the patient application determining that the patient is not properly using the at least one monitoring device: notifying the patient via at least one of an audible alert, a visual alert and a vibrational alert via the at least one patient device; and temporarily suspending future dosages of the pills until the patient application determines that the patient is properly using the at least one monitoring device.

34. The pill dispensing system according to embodiments 18-33, wherein the at least one pill magazine is spring-loaded.

35. The pill dispensing system according to embodiments 18-34, wherein the at least one pill magazine is in mechanical communication with a drive shaft positioned and configured for ejecting at least one pill from said pill magazine through the pill outlet of the at least one pill storage container.

36. The pill dispensing system according to embodiments 18-35, wherein the at least one pill storage container further provides: an at least one power source in electrical communication with a solenoid; and a magazine drive shaft in operable connection with the drive shaft which, in turn, is in operable connection with the solenoid.

37. The pill dispensing system according to embodiments 18-36, wherein the at least one power source is a battery.

38. The pill dispensing system according to embodiments 18-37, wherein the housing of the at least one pill storage container further provides a selectively lockable outlet cover positioned and configured for selectively restricting access to the pill outlet.

In closing, regarding the exemplary embodiments of the present invention as shown and described herein, it will be appreciated that a tamper-proof pill dispenser system, along with associated methods of use, is disclosed. Because the principles of the invention may be practiced in a number of configurations beyond those shown and described, it is to be understood that the invention is not in any way limited by the exemplary embodiments and is able to take numerous forms without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention. Furthermore, the various features of each of the above-described embodiments may be combined in any logical manner and are intended to be included within the scope of the present invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein. Similarly, as used herein, unless indicated to the contrary, the term "substantially" is a term of degree intended to indicate an approximation of the characteristic, item, quantity, parameter, property, or term so qualified, encompassing a range that can be understood and construed by those of ordinary skill in the art.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment.

The methods as described above may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multi-chip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A method for administering a pill dispensing system for managing the distribution of pills to a patient, the method comprising the steps of:
    implementing an at least one tamper-proof pill storage container that provides an at least one pill magazine positioned within a housing of the pill storage container and configured for storing and selectively dispensing a plurality of pills through a pill outlet provided by the housing;
    implementing a patient application residing in memory on an at least one patient device under the control of the patient, the patient application in selective communication with the at least one pill storage container;
    implementing an at least one monitoring device in selective communication with the patient application, the at least one monitoring device configured for assisting the patient application with monitoring an at least one vital of the patient;
    obtaining from the patient at least one of a security code, via the patient application, and an at least one biometric marker associated with the patient, via an at least one biometric sensor;
    registering, via the patient application, a prescription associated with the pills contained within the at least one pill magazine of the at least one pill storage container, said prescription including a dosage interval and a dosage quantity;
    upon the patient application determining that a dosage of the pills is available for the patient, based on the associated dosage interval:
        obtaining from the patient at least one of the security code and the at least one biometric marker; and
        upon the patient application authenticating at least one of the security code and the at least one biometric marker:
            distributing a quantity of pills equal to the associated dosage quantity; and
            upon said pill storage container distributing the pills to the patient, scheduling, via the patient application, a future dosage of the pills based on the associated dosage interval;
    upon the patient application determining that the at least one monitored vital is abnormal:
        notifying the patient via the at least one patient device;
        upon the patient application failing to receive a response from the patient within a pre-defined period of time, automatically alerting, via the patient application, local emergency personnel; and
    upon the at least one pill storage container being tampered with, said pill storage container automatically releasing an at least one tamper-proof substance within said pill storage container in order to render the pills inert, inactive or intolerable.

2. The method of claim 1, wherein the step of obtaining an at least one biometric marker associated with the patient further comprises the step of obtaining at least one of a fingerprint of the patient, a facial image of the patient, a retinal image of the patient, and an iris image of the patient.

3. The method of claim 1, wherein the step of registering a prescription associated with the pills further comprises the step of processing, via the patient application, a unique prescription code associated with the pills, said prescription code containing the dosage interval and the dosage quantity.

4. The method of claim 3, wherein the step of processing a unique prescription code associated with the pills further comprises the step of scanning a visual barcode associated with the pills using a camera of the at least one patient device, said visual barcode containing the dosage interval and the dosage quantity.

5. The method of claim 3, further comprising the step of encrypting, via the patient application, each of the biometric marker, security code and prescription code with a unique hash value to be stored in each of the at least one patient device and the associated at least one pill storage container, thereby establishing a unique link therebetween.

6. The method of claim 1, wherein the step of distributing a quantity of pills equal to the associated dosage quantity further comprises the step of requiring the patient to activate an actuator positioned on the housing of said pill storage container in order for the pills to be distributed.

7. The method of claim 1, further comprising the step of, upon said pill storage container distributing the pills to the patient, recording, via the patient application, a date, time and dosage quantity associated with the distributed pills.

8. The method of claim 1, wherein the patient application is further in selective communication with an at least one clinician device under the control of a clinician tasked with monitoring the patient's proper consumption of the pills, the at least one clinician device capable of receiving data related to the distribution of pills to the patient, as well as transmitting dosage interval and dosage quantity changes to the patient application.

9. The method of claim 8, wherein the step of the patient application determining that the at least one monitored vital is abnormal further comprises the step of notifying the at least one clinician device, via the patient application, of the abnormal vital.

10. The method of claim 8, further comprising the step of, upon the patient application determining that the at least one pill magazine of the at least one pill storage container is empty or running low, automatically notifying at least one of the patient and clinician that a new prescription or refill is required.

11. The method of claim 1, wherein the step of the at least one pill storage container releasing an at least one tamper-proof substance further comprises the step of releasing cyanoacrylate.

12. The method of claim 1, wherein the step of the at least one pill storage container releasing an at least one tamper-proof substance further comprises the step of releasing methyl methacrylate.

13. The method of claim 1, wherein the step of implementing an at least one monitoring device further comprises the step of implementing an at least one respiratory monitor positioned and configured for obtaining a breathing rate of the patient.

14. The method of claim 1, further comprising the step of, upon the patient application determining that the patient is not properly using the at least one monitoring device:
   notifying the patient via at least one of an audible alert, a visual alert and a vibrational alert via the at least one patient device; and
   temporarily suspending future dosages of the pills until the patient application determines that the patient is properly using the at least one monitoring device.

15. The method of claim 1, further comprising the step of, upon the patient application determining that the at least one monitored vital is abnormal, temporarily suspending future dosages of the pills until the patient application determines that said monitored vital has returned to normal.

16. A method for administering a pill dispensing system for managing the distribution of pills to a patient, the method comprising the steps of:
   implementing an at least one tamper-proof pill storage container that provides an at least one pill magazine positioned within a housing of the pill storage container and configured for storing and selectively dispensing a plurality of pills through a pill outlet provided by the housing;
   implementing a patient application residing in memory on an at least one patient device under the control of the patient, the patient application in selective communication with the at least one pill storage container;
   implementing an at least one respiratory monitor in selective communication with the patient application, the at least one respiratory monitor configured for assisting the patient application with monitoring a breathing rate of the patient;
   obtaining from the patient at least one of a security code, via the patient application, and an at least one biometric marker associated with the patient, via an at least one biometric sensor;
   registering, via the patient application, a prescription associated with the pills contained within the at least one pill magazine of the at least one pill storage container, said prescription including a dosage interval and a dosage quantity;
   upon the patient application determining that a dosage of the pills is available for the patient, based on the associated dosage interval:
      obtaining from the patient at least one of the security code and the at least one biometric marker; and
      upon the patient application authenticating at least one of the security code and the at least one biometric marker:
         distributing a quantity of pills equal to the associated dosage quantity; and
         upon said pill storage container distributing the pills to the patient, scheduling, via the patient application, a future dosage of the pills based on the associated dosage interval;
   upon the patient application determining that the breathing rate of the patient is abnormal:
      notifying the patient via at least one of an audible alert, a visual alert and a vibrational alert via the at least one patient device; and
      upon the patient application failing to receive a response from the patient within a pre-defined period of time, automatically alerting, via the patient application, local emergency personnel; and
   upon the at least one pill storage container being tampered with, said pill storage container automatically releasing an at least one tamper-proof substance within said pill storage container in order to render the pills inert, inactive or intolerable.

17. A pill dispensing system for managing the distribution of pills to a patient, the system comprising:
   an at least one tamper-proof pill storage container that provides an at least one pill magazine positioned within a housing of the pill storage container and configured for storing and selectively dispensing a plurality of pills through a pill outlet provided by the housing;
   a patient application residing in memory on an at least one patient device under the control of the patient, the patient application in selective communication with the at least one pill storage container; and
   an at least one respiratory monitor in selective communication with the patient application, the at least one respiratory monitor positioned and configured for obtaining a breathing rate of the patient;
   wherein, upon the patient desiring to utilize the system to manage the distribution of pills, the system is configured for:
      obtaining from the patient at least one of a security code, via the patient application, and an at least one biometric marker associated with the patient, via an at least one biometric sensor;
      registering, via the patient application, a prescription associated with the pills contained within the at least one pill magazine of the at least one pill storage container, said prescription including a dosage interval and a dosage quantity;

upon the patient application determining that a dosage of the pills is available for the patient, based on the associated dosage interval:
  obtaining from the patient at least one of the security code and the at least one biometric marker; and
  upon the patient application authenticating at least one of the security code and the at least one biometric marker:
    distributing a quantity of pills equal to the associated dosage quantity; and
    upon said pill storage container distributing the pills to the patient, scheduling, via the patient application, a future dosage of the pills based on the associated dosage interval; and
upon the patient application determining that the breathing rate of the patient is abnormal:
  notifying the patient via at least one of an audible alert, a visual alert and a vibrational alert via the at least one patient device; and
  upon the patient application failing to receive a response from the patient within a pre-defined period of time, automatically alerting, via the patient application, local emergency personnel.

18. The pill dispensing system of claim 17, wherein upon the at least one pill storage container being tampered with, the system is further configured for automatically releasing an at least one tamper-proof substance within said pill storage container in order to render the pills inert, inactive or intolerable.

19. The pill dispensing system of claim 17, wherein the patient application is further in selective communication with an at least one clinician device under the control of a clinician tasked with monitoring the patient's proper consumption of the pills, the at least one clinician device capable of receiving data related to the distribution of pills to the patient, as well as transmitting dosage interval and dosage quantity changes to the patient application.

20. The pill dispensing system of claim 17, wherein the housing of the at least one pill storage container further provides a selectively lockable outlet cover positioned and configured for selectively restricting access to the pill outlet.

* * * * *